United States Patent
Nishinakamura et al.

(10) Patent No.: US 10,072,249 B2
(45) Date of Patent: Sep. 11, 2018

(54) METHOD OF INDUCING KIDNEY FROM PLURIPOTENT STEM CELLS

(71) Applicant: NATIONAL UNIVERSITY CORPORATION KUMAMOTO UNIVERSITY, Kumamoto (JP)

(72) Inventors: Ryuichi Nishinakamura, Kumamoto (JP); Atsuhiro Taguchi, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 2 days.

(21) Appl. No.: 15/026,462

(22) PCT Filed: Oct. 16, 2014

(86) PCT No.: PCT/JP2014/077601
§ 371 (c)(1),
(2) Date: Jul. 8, 2016

(87) PCT Pub. No.: WO2015/056756
PCT Pub. Date: Apr. 23, 2015

(65) Prior Publication Data
US 2016/0304838 A1 Oct. 20, 2016

(30) Foreign Application Priority Data

Oct. 18, 2013 (JP) ................. 2013-217029

(51) Int. Cl.
| | | |
|---|---|---|
| *C12N 5/00* | (2006.01) | |
| *A01N 61/00* | (2006.01) | |
| *C07K 1/00* | (2006.01) | |
| *C07K 14/50* | (2006.01) | |
| *C07K 14/51* | (2006.01) | |
| *C12N 5/071* | (2010.01) | |

(52) U.S. Cl.
CPC ......... *C12N 5/0671* (2013.01); *C12N 5/0672* (2013.01); *C12N 2501/119* (2013.01); *C12N 2501/155* (2013.01); *C12N 2501/16* (2013.01); *C12N 2501/385* (2013.01); *C12N 2501/415* (2013.01); *C12N 2506/02* (2013.01); *C12N 2506/45* (2013.01)

(58) Field of Classification Search
CPC ............ C12N 5/0672; C12N 2501/119; C12N 2501/16; C12N 2501/155; C12N 2501/415; C12N 2506/02; C12N 2506/45
USPC ................ 435/377; 514/1, 8.8, 9.1; 530/350
See application file for complete search history.

(56) References Cited

U.S. PATENT DOCUMENTS

2007/0031966 A1  2/2007  Dressler et al.

FOREIGN PATENT DOCUMENTS

| JP | 2013-530680 A | 8/2013 |
| WO | 2012/011610 A1 | 1/2012 |
| WO | WO2012/013969 A1 | 2/2012 |
| WO | 2013/094771 A1 | 6/2013 |

OTHER PUBLICATIONS

Little et al., 2016, US 20160237409, effective filing date, Jun. 14, 2013.*
Narsinh et al., 2011, Molecular Therapy, vol. 9, No. 4, p. 635-638.*
Bellin et al., 2012, Nature reviews/Molecular Cell Biology, vol. 13, p. 713-726.*
Burridge et al., 2011, PLoS ONE, vol. 6, No. 4, e18293, p. 1-16.*
Wang, Yigang, 2014, New Journal of Science, vol. 2014, Article ID 756240, pp. 1-22.*
A. Aulehla et al: "Signaling Gradients during Paraxial Mesoderm Development", Cold Spring Harbor Perspectives in Biology, vol. 2, No. 2, Feb. 1, 2010 (Feb. 1, 2010), pp. a000869-a000869.
Daichi Toyoda et al: "Sall4 Is Transiently Expressed in the Caudal Wolffian Duct and the Ureteric Bud, but Dispensable for Kidney Development", PLOS ONE, vol. 8, No. 6, Jun. 18, 2013 (Jun. 18, 2013).
Karthikeyan Narayanan et al: "Human embryonic stem cells differentiate into functional renal proximal tubular-like cells", Kidney International, vol. 83, No. 4, Feb. 6, 2013 (Feb. 6, 2013), pp. 593-603.
Ryuichi Nishinakamura et al; "Nephron progenitors in the metanephric mesenchyme", Pediatric Nephrology., vol. 26. No. 9, Sep. 1, 2011 (Sep. 1, 2011), pp. 1463-146.

(Continued)

*Primary Examiner* — Shin Lin Chen
(74) *Attorney, Agent, or Firm* — Hunton Andrews Kurth LLP

(57) ABSTRACT

The purpose of the present invention is to provide a process or method that can be utilized when deriving a three-dimensional structure of a kidney from pluripotent stem cells such as ES cells or iPS cells. The differentiation inducing method is characterized by culturing pluripotent cells with the following three steps, in order: (a) a step of culturing an embryoid body induced from the pluripotent stem cells in medium containing Bmp4 and a high-concentration (concentration A) Wnt agonist; (b) a step of culturing the embryoid body in medium which contains activin, Bmp4, retinoic acid and a middle-concentration (concentration B) Wnt agonist; and (c) a step of culturing the embryoid body in medium containing Fgf9 and a low-concentration (concentration C) Wnt agonist (herein, the Wnt agonist concentrations is concentration A>concentration B>concentration C).

14 Claims, 22 Drawing Sheets

(56) References Cited

OTHER PUBLICATIONS

Supplementary European Search Report dated Feb. 21, 2017 (correspondent EP Application No. 14853879).
International Search Report and International Preliminary Report on Patentability of International Application No. PCT/JP2014/077601 dated Nov. 18, 2014.
Mugford, et al., "Osr1 expression demarcates a multi-potent population of intermediate mesoderm that undergoes progressive restriction to an Osr1-dependent nephron progenitor compartment within the mammalian kidney", Developmental Biology 324, (2008), pp. 88-98.
Mugford, et al., "Hoxd11 specifies a program of metanephric kidney development within the intermediate mesoderm of the mouse embryo", Developmental Biology 319, (2008), pp. 396-405.
Wellik, et al., "Hox11 paralogous genes are essential for metanephric kidney induction", Genes Dev. 16, (2002) pp. 1423-1432.
Osafune, et al., "Identification of multipotent progenitors in the embryonic mouse kidney by a novel colony-forming assay", Development 133, (2006), pp. 151-161.
Takemoto, et al., "Tbx6-dependent Sox2 regulation determines neural or mesodermal fate in axial stem cells", Nature 470, (2011), pp. 394-398.
Tzouanacou, et al., "Redefining the Progression of Lineage Segregations during Mammalian Embryogenesis by Clonal Analysis", Dev Cell 17, (2009), pp. 365-376.
Wilson, et al., "Stem cells, signals and vertebrate body axis extension", Development 136, (2009), pp. 1591-1604.
Kispert, et al., "Wnt-4 is a mesenchymal signal for epithelial transformation of metanephric mesenchyme in the developing kidney", Development 125, (1998), pp. 4225-4234.
Nishinakamura, et al., "Murine homolog of SALL1 is essential for ureteric bud invasion in kidney development", Development 128, (2001), pp. 3105-3115.
James, et al., "Odd-skipped related 1 is required for development of the metanephric kidney and regulates formation and differentiation of kidney precursor cells", Development 133, (2006), pp. 2995-3004.
Barak, et al., "FGF9 and FGF20 Maintain the Stemness of Nephron Progenitors in Mice and Man", Dev Cell 22, (2012), pp. 1191-1207.
Poladia, et al., "Role of fibroblast growth factor receptors 1 and 2 in the metanephric mesenchyme", Developmental Biology 291, (2006), pp. 325-339.
Atsuta, et al., "Transgenesis of the Wolffian duct visualizes dynamic behavior of cells undergoing tubulogenesis in vivo", Develop. Growth Differ. 55, (2013), pp. 579-590.
Attia, et al., "Analysis of nephric duct specification in the avian embryo", Development 139, (2012), pp. 4143-4151.

Obara-Ishihara, et al., "The surface ectoderm is essential for nephric duct formation in intermediate mesoderm", Development 126, (1999), pp. 1103-1108.
Saxen, Organogenesis of the Kidney, (New York: Cambridge University Press), (1987), <http://ebooks.cambridge.org/ebook.jsf?bid=CBO9780511565083>, online publication date: Oct. 2009, accessed date: Jul. 7, 2016.
Hermann, et al., "Cloning of the T gene required in mesoderm formation on the mouse", Nature 343, (1990), pp. 617-622.
Burridge, et al., "Production of De Novo Cardiomyocytes: Human Pluripotent Stem Cell Differentiation and Direct Reprogramming", Cell Stem Cell 10, (2012), pp. 16-28.
Bernardo, et al., "Brachyury and CDX2 Mediate BMP-Induced Differentiation of Human and Mouse Pluripotent Stem Cells into Embryonic and Extraembryonic Lineages", Cell Stem Cell 9, (2011), pp. 144-155.
Kattman, et al., "Stage-Specific Optimization of Activin/Nodal and BMP Signaling Promotes Cardiac Differentiation of Mouse and Human Pluripotent Stem Cell Lines", Cell Stem Cell 8, (2011), pp. 228-240.
Yu, et al., "FGF2 Sustains NANOG and Switches the Outcome of BMP4-Induced Human Embryonic Stem Cell Differentiation", Cell Stem Cell 8, (2011), pp. 326-334.
International Society for Stem Cell Research poster abstracts, Jun. 12, 2013, 11th, F-2184, <http://www.isscr.org/docs/default-source/am2013-support-documents/isscr2013-posterabstracts.pdf>.
Daiwa Shoken Health Zaidan no Josei ni yoru . . . Kenkyu Gyosekishu, Mar. 1, 2013, 36th series, 37 to 42 (in Japanese).
Japanese Journal of Pediatric Nephrology, Apr. 15, 2013, 26, 1, 64 to 69 (in Japanese).
Asanuma, J pharmacol sci, Mar. 15, 2013, 121 supplement1, S1C-6-4.
Mae, et al., "Monitoring and robust induction of nephrogenic intermediate mesoderm from human pluripotent stem cells", Nature Communications, Jan. 22, 2013, 4, 1367.
Naibunpitsu•Tonyobyo•Taisha Naika, (2012), 35, 2, pp. 125-129 (in Japanese).
Nishikawa, et al., "Stepwise renal lineage differentiation of mouse embryonic sem cells tracing in vivo development", Biochemical and Biophysical Research Communications, (2012), 417, pp. 897-902.
Nephrology Frontier, 10, 3, 2011, pp. 238-241 (in Japanese).
Taguchi, et al. "Redifining the In Vivo Origin of Metanephric Nephron Progenitors Enables Generation of Complex Kidney Strcutures from Pluripotent Stem Cells", Cell Stem Cell, (2014), 14, pp. 53-67.
Seitai no Kagaku, Jun. 15, 2014, 65, 3, pp. 244-248 (in Japanese).
Araoka, et al., "Efficient and Rapdi Induction of Human iPSCs/ESCs into Nephrogenic Intermediate Mesoderm Using Small Molecule-Based Differentiation Methods", PLOS one, (2014), 9, 1, e84881.

\* cited by examiner

Fig. 14

|  | E8.5 | | E9.5 | | | E11.5 MM | |
| --- | --- | --- | --- | --- | --- | --- | --- |
|  | GFP+ | GFP- | GFP+ | | GFP- | GFP+ | |
|  | | | Itga8+ Pdgfra- | others | | Itga8+ Pdgfra- | others |
| Osr1 | 0.92 | | 1.09 | 0 | | 1.68 | -1.73 |
| Itga8 | 0 | -1.08 | 3.01 | 1.08 | -0.44 | 3.67 | -0.44 |
| Pdgfra | 1.37 | 0 | -2.56 | 1.42 | -0.03 | -5.69 | 2.01 |
| Wt1 | -4.25 | -6.21 | 1.88 | 0 | -3.71 | 2.04 | 1.14 |
| Pax2 | 0 | -0.63 | 2.29 | 0.19 | -0.31 | 2.99 | -0.25 |
| Six2 | -1.22 | | 3.91 | 0.13 | 0 | 6.83 | -0.83 |
| Gdnf | | | 3.24 | 0 | | 3.83 | 1.55 |
| Sall1 | 0.03 | -0.99 | 0.70 | -0.94 | 0 | 1.01 | -0.94 |
| Sall2 | -0.78 | -1.71 | 0.76 | -0.49 | 0 | 1.20 | 0.15 |
| Crym | 0 | | 4.67 | 1.48 | -2.06 | 5.26 | |
| Eya4 | | | 2.10 | 0 | -0.45 | 4.74 | 3.17 |
| Foxd2 | -1.62 | -0.96 | 1.40 | -0.63 | 0 | 3.07 | 0.62 |
| Foxc1 | -0.38 | -0.87 | 0.57 | -0.50 | 0 | 0.87 | 2.06 |
| Foxc2 | -0.33 | -0.50 | 0.74 | -0.77 | 0 | 1.35 | 1.60 |
| Gfra1 | | | 3.32 | 0.19 | | 4.26 | |
| Ncam1 | -1.53 | -1.44 | 0.94 | -1.05 | 0 | 1.26 | 0.17 |
| Hoxa10 | -1.56 | -2.81 | 0 | 0.39 | -0.17 | 2.37 | 1.93 |
| Hoxa11 | -0.58 | -1.58 | -0.04 | 0.88 | 0 | 2.56 | 1.71 |
| Hoxc10 | -3.00 | -5.03 | 0.13 | -0.28 | 0 | 1.02 | 0.81 |
| Hoxd10 | -2.59 | | -1.41 | 0.27 | 0 | 1.51 | 1.58 |
| Hoxd11 | -2.16 | -3.19 | -2.14 | 1.15 | 0 | 3.05 | 2.66 |
| Hoxd12 | -2.09 | -2.27 | -1.40 | 0 | 0.44 | 1.84 | 1.26 |
| Hoxc9 | -0.34 | -2.20 | 1.19 | 0 | 0.61 | 0.09 | -0.16 | colony forming ratio (%)

|  |  | E8.5 | | E9.5 | | | E11.5 MM | |
|---|---|---|---|---|---|---|---|---|
|  |  | GFP+ | GFP- | GFP+ | | GFP- | GFP+ | |
|  |  |  |  | Itga8+ Pdgfra- | ohters |  | Itga8+ Pdgfra- | others |
| Fgf ligands | Fgf9 | 0.4903765 | -1.72 | 2.19 | 0 | -2.24 | 0.70 |  |
|  | Fgf20 |  |  | 4.62 | 1.39 |  | 5.24 |  |
| Fgf receptors | Fgfr1 | -0.00 | -0.89 | 0.35 | 0.17 | -0.43 | 1.31 | 0 |
|  | Fgfr2 | -1.06 | -1.31 | 0.08 | -0.32 | 0 | 0.91 | 0.20 |
| Fgf targets | Spry1 | -1.34 | -1.19 | 1.10 | 0.44 | -0.25 | 1.05 | 0 |
|  | Etv4 | 0.45 | -0.02 | 0.94 | -0.01 | 0 | 1.81 | -0.82 |
|  | Etv5 | 0.46 | -0.83 | 0.56 | 0 | -0.46 | 0.83 | -1.03 |
| Bmp targets | Msx1 | 1.29 | 0.22 | -1.06 | 0.69 | 0 | -1.89 | -1.53 |
|  | Msx2 | 2.00 | 0.18 | -2.00 | 1.22 | 0 | -2.76 | -3.68 |
|  | Id1 | 0.31 | -1.09 | 0 | 0.60 | -0.71 | -0.32 | 0.34 |
| Wnt target | Axin2 | 1.50 | 0 | -0.74 | 0.89 | 0.86 | -0.65 | -1.46 |

METHOD OF INDUCING KIDNEY FROM PLURIPOTENT STEM CELLS

CROSS-REFERENCE TO RELATED APPLICATIONS

The present application is a National Stage of PCT Application No. PCT/JP2014/077601, filed Oct. 16, 2014, which claims priority to Japanese Application No. JP 2013-217029 filed Oct. 18, 2013. The entirety of the aforementioned applications is incorporated herein by reference.

TECHNICAL FIELD

The present invention relates to a method of inducing a kidney from a pluripotent stem cell. More particularly, the present invention relates to a method of inducing a three-dimensional structure of the kidney including both of a glomerulus and a renal tubule, from a pluripotent stem cell, for example, an ES cell and an iPS cell.

BACKGROUND ART

The kidney excretes waste products by producing urine and, at the same time, plays an important role in maintaining homeostasis of electrolytes and water in a body. When the kidney function is lost, since water and a variety of toxic components are accumulated, and clouding of consciousness, dyspnea due to lung edema, or hyperpotassemia results in death, it is necessary to conduct artificial dialysis. The number of patients undergoing artificial dialysis in Japan has reached about 300 thousands, and is also steadily increasing currently. The primary cause for artificial dialysis introduction is diabetes which occupies about 45% of the number of introduction patients. In addition, the kidney also plays an important role as an endocrine organ, regulates blood pressure by producing renin, and is involved in bone metabolism and maintenance of erythrocytes by activation of vitamin D and production of erythropoietin. For this reason, in renal failure, abnormality of blood pressure and a bone, and severe anemia are seen. For anemia associated with renal failure, treatment by administering erythropoietin a few times per week is performed currently, but administration throughout the life is necessary, and this causes an increase in medical expenses.

When patients have fallen into end-stage renal failure due to a kidney disease such as diabetic nephropathy, chronic glomerular nephritis, renal sclerosis etc., two therapeutic methods: kidney transplantation from corpses and living bodies and artificial dialysis through blood or peritoneum are conducted. Kidney transplantation is fundamental treatment which can completely compensate for the damaged renal function, but it could not have become a general therapeutic method due to chronic deficiency of donors. On the other hand, artificial dialysis imposes severe dietary restriction or periodic hospital visit on patients, while since it is mere compensation for the filtration function of the kidney, it causes long term complication. As the new treatment to replace them, regenerative medicine is paid attention.

Although in vitro construction of a variety of types of tissues from pluripotent stem cells has been successful, there has still been no successful case of in vitro nephrogenesis, and establishment of methodology thereof has been waited. This is mainly due to that details of the mechanism thereof have not been clarified due to the embryological complexity of an in vivo renal differentiation process. That is, unlike other main organs, the kidney is formed via a complicated process associated with formation of three primordia: two temporary primordia (pronephros, mesonephros) located anteriorly, and further, metanephros located posteriorly and differentiating into the adult kidney, in its developmental process. Furthermore, in order that the artificially reconstructed kidney functions, essential construction of a three-dimensional structure including both the "glomerulus" and the "renal tubule", constituting a "nephron" which is its functional unit further enhances its technical difficulty.

The kidney is developed from the metanephros which develops at the most posterior part of the fetal body trunk. The metanephros is formed by interaction between two precursor tissues, that is, the metanephric mesenchyme and the ureteric bud. Previously, it has been shown by cell lineage analysis that both of the metanephric mesenchyme and the ureteric bud are developed from the intermediate mesoderm expressing a transcription factor, Osrl, which appears at day 8.5 of the viviparity (E) (Non-Patent Literature 1: Mugford et al., Dev Biol 324, 88-98, 2008). However, the mechanism which is a basis of by what growth factor signal the initial stage mesoderm is differentiated into the intermediate mesoderm has not been revealed. In addition, in a process in which the intermediate mesoderm is developed into the metanephros, the importance of a posterior Hox gene group posterior to the intermediate mesoderm has been reported (Non-Patent Literature 2: Mugford et al., Dev Biol 319, 396-405, 2008; Non-Patent Literature 3: Wellik et al., Genes Dev 16, 1423-1432, 2002). However, how the anterior-posterior axis is formed in the intermediate mesoderm, a posterior Hox gene is developed, and the metanephric mesenchyme is formed (posteriorization) has not been clarified yet.

The kidney is formed by interaction of two tissues of the metanephric mesenchyme and the ureteric bud derived from the mesoderm, and a main structure such as the "glomerulus" and the "renal tubule" contained in the nephron which is its functional unit is derived from the former (metanephric mesenchyme). The inventors have previously reported that a progenitor cell (metanephric nephron progenitor cell) which is the source of the nephron exists in the metanephric mesenchyme at a mouse fetal stage, and also developed a method of detecting it (Non-Patent Literature 4: Osafune, Nishinakamura et al., Development 133, 151-161, 2006). In addition, a method of inducing the intermediate mesoderm from an iPS cell, by culturing the iPS cell in the presence of activin A and Wnt, then, culturing the cell in the presence of BMP and Wnt has been reported (Patent Literature 1: international publication: WO2012/011610). However, there is no report that the induction of the "metanephric nephron progenitor cell" which can reconstruct both of the glomerulus and the renal tubule from pluripotent stem cells has been succeeded.

CITATION LIST

Patent Literature

Patent Literature 1: International Publication WO2012/011610

Non-Patent Literature

Non-Patent Literature 1: Mugford et al., Dev Biol 324, 88-98, 2008
Non-Patent Literature 2: Mugford et al., Dev Biol 319, 396-405, 2008

Non-Patent Literature 3: Wellik et al., Genes Dev 16, 1423-1432, 2002
Non-Patent Literature 4: Osafune et al., Development 133, 151-161, 2006
Non-Patent Literature 5: Takemoto et al., Nature 470, 394-398, 2011
Non-Patent Literature 6: Tzouanacou et al., Dev Cell 17, 365-376, 2009
Non-Patent Literature 7: Wilson et al., Development 136, 1591-1604, 2009
Non-Patent Literature 8: Kispert et al., Development 125, 4225-4234, 1998
Non-Patent Literature 9: Nishinakamura et al., Development 128, 3105-3115, 2001
Non-Patent Literature 10: James et al., Development 133, 2995-3004, 2006
Non-Patent Literature 11: Barak et al., Dev Cell 22, 1191-1207, 2012
Non-Patent Literature 12: Poladia et al., Dev Biol 291, 325-339, 2006
Non-Patent Literature 13: Atsuta et al., Dev Growth Differ 55, 579-590, 2013
Non-Patent Literature 14: Attia et al., Development 139, 4143-4151, 2012
Non-Patent Literature 15: Obara-Ishihara et al., Development 126, 1103-1108, 1999
Non-Patent Literature 16: Saxen, Organogenesis of the Kidney (New York: Cambridge University Press) (1987)
Non-Patent Literature 17: Herrmann et al., Nature 343, 617-622, 1990
Non-Patent Literature 18: Burridge, Cell Stem Cell 10, 16-28, 2012
Non-Patent Literature 19: Bernard et al., Cell Stem Cell 9, 144-155, 2011
Non-Patent Literature 20: Kattman et al., Cell stem cell 8, 228-240, 2011
Non-Patent Literature 21: Yu et al., Cell Stem Cell 8, 326-334, 2011

SUMMARY OF THE INVENTION

Technical Problem

An object of the present invention is to provide a step or a method which can be used when a three-dimensional structure of the kidney is induced from a pluripotent stem cell, for example, an ES cell or an iPS cell. An object of present invention is, particularly, to provide a method of first inducing an intermediate mesoderm cell from the ES cell or the iPS cell (e.g. mouse embryonic stem cell and human artificial pluripotent stem (iPS) cell), and further, inducing a metanephric mesenchyme cell (metanephric nephron progenitor cell) from the intermediate mesoderm cell, as well as a new model of the kidney differentiation lineage using such a method.

Solution to Problem

In order to solve the aforementioned problems, the present inventors intensively continued study, and as a result, succeeded in inducing a metanephric nephron progenitor cell (metanephric mesenchyme) which can reconstruct a three-dimensional structure of the kidney, that is, the renal tubule and the glomerulus, from mouse and human pluripotent stem cells, resulting in completion of the present invention. A majority of podocytes constituting the kidney are derived from metanephric mesenchymal cells contained in the metanephros located at the posterior end of the body trunk. However, in vivo, since development passes through a complicated developmental process including formation of the pronephros and the mesonephros, prior to development of the metanephros, this has made an in vitro attempt of kidney regeneration difficult. The present inventors confirmed that a progenitor of the metanephric mesenchymal cell is maintained in the state of the undifferentiated mesoderm which expresses a transcription factor, Brachyury (=T), until a term of termination of gastrulation in vivo, and is posteriorized. And, the inventors found that a T-positive cell which has been sorted from a mouse embryo is differentiated into the metanephric mesenchyme in vitro by posteriorization using Wnt agonist at a high concentration, subsequent step-wise reduction in an amount of the Wnt agonist, and addition of each term-specific growth factor. When mouse and human pluripotent stem cells are treated similarly, metanephric mesenchymal cells are obtained, and they can reconstruct a three-dimensional structure of the kidney, including glomeruli with podocytes and renal tubules with clear lumina, resulting in completion of the present invention. The present invention enabled reconstruction of the kidney.

The present invention includes the following:

(1) A method of differentiation-inducing a pluripotent stem cell derived from a mammal into a metanephric mesenchyme which is a (metanephric) nephron progenitor cell, the method comprising the following three steps:
(a) a step of culturing an embryoid body which has been induced from the pluripotent stem cell in a culture medium containing Bmp, and Wnt agonist at a high concentration (concentration A),
(b) a step of culturing the embryoid body in a culture medium containing Bmp, and Wnt agonist at an intermediate concentration (concentration B), and
(c) a step of culturing the embryoid body in a culture medium containing Fgf, and Wnt agonist at a low concentration (concentration C), in this order,
(wherein a concentration of the Wnt agonist is concentration A>concentration B>concentration C, and a concentration A is at least five times of a concentration C).
(2) The differentiation-inducing method according to (1), wherein the concentrations of the Wnt agonist in the steps (a), (b) and (c) are such that a concentration A is at least two times (preferably, at least three times) of a concentration B, and a concentration B is at least two times (preferably, at least three times) of a concentration C.
(3) The differentiation-inducing method according to (1) or (2), wherein the medium in the step (b) further comprises activin.
(4) The differentiation-inducing method according to (3), wherein the medium in the step (b) further comprises retinoic acid.
(5) The differentiation-inducing method according to any one of (1) to (4), wherein the Wnt agonist is a GSK-3 inhibitor (provided that Wnt agonists at respective steps may be same or different).
(6) The differentiation-inducing method according to (5), wherein the Wnt agonist is selected from the group consisting of CHIR99021, BIO, and SB415286 (provided that Wnt agonists at respective steps may be the same or different).
(7) The differentiation-inducing method according to any one of (1) to (6), wherein the Bmp is selected from the group consisting of the Bmp family, preferably, a group consisting of Bmp2, Bmp4 and Bmp7, and the Fgf is selected from the group consisting of the Fgf family, preferably, a group consisting of Fgf 2, Fgf 9 and Fgf20.

(8) The differentiation-inducing method according to any one of (1) to (7), wherein the Bmp is Bmp4, and the Fgf is Fgf9.

(9) The differentiation-inducing method according to any one of (1) to (8), wherein the Wnt agonist in the steps (a), (b) and (c) is CHIR99021, and a concentration A is 7.5 µM to 15 µM, and a concentration C is 0.5 µM to 2.0 µM.

(10) The differentiation-inducing method according to (9), wherein the Bmp in the steps (a) and (b) is Bmp4, and a concentration thereof in the step (a) is 0.1 ng/ml to 3 ng/ml, and a concentration thereof in the step (b) is 1 ng/ml to 10 ng/ml.

(11) The differentiation-inducing method according to (10), wherein activin is contained at a concentration of 2.5 to 40 ng/mL, in the step (b).

(12) The differentiation-inducing method according to any one of (1) to (11), wherein the steps (a), (b) and (c) are continuous steps.

(13) The differentiation-inducing method according to any one of (1) to (12), wherein the medium in the step (c) contains none of Bmp, retinoic acid and activin.

(14) The differentiation-inducing method according to any one of (1) to (13), wherein the pluripotent stem cell is a mouse ES cell or a mouse iPS cell, or a human ES cell or a human iPS cell.

(15) The differentiation-inducing method according to (14), wherein the pluripotent stem cell is a human iPS cell.

(16) The differentiation-inducing method according to (14), wherein the pluripotent stem cell is the mouse ES cell or the mouse iPS cell, and the step (a) is a step of culturing the embryoid body for at least one day or longer and four days or shorter (wherein, preferably, the medium is exchanged with fresh medium at least once).

(17) The differentiation-inducing method according to (14), wherein the pluripotent stem cell is the human ES cell or the human iPS cell, and the step (a) is a step of culturing the embryoid body for at least three days or longer and eleven days or shorter (wherein, preferably, the medium is exchanged with fresh medium at least two times).

(18) A nephron progenitor cell differentiation-inducted from a pluripotent stem cell derived from a mammal, characterized in that the nephron progenitor cell is a cell population expressing all of transcription factors, Osr1, Wt1, Pax2, Six2, Hoxa10, and Hoxa11.

(19) The nephron progenitor cell according to (18), wherein the pluripotent stem cell is a mouse ES cell or a mouse iPS cell, or a human ES cell or a human iPS cell.

(20) A nephron progenitor cell, which was induced by the differentiation-inducing method according to any one of (1) to (17).

(21) A method of making a three-dimensional kidney structure having a glomerulus and a renal tubule, comprising using a nephron progenitor cell according to any one of (18) to (20).

(22) The method of making a three-dimensional kidney according to (21), wherein the method comprises coculturing the nephron progenitor cell with embryonic spinal cord or a Wnt4-expressing cell at an air-liquid interface.

(23) A three-dimensional kidney structure having a glomerulus and a renal tubule, which was formed by the method according to (21) or (22).

(24) A proximal renal tubular cell, characterized in that the cell is a cell population expressing Cadherin 6, Megalin, and LTL, which was differentiation-induced from a nephron progenitor cell according to any one of (18) to (20).

(25) The proximal renal tubular cell according to (24), wherein the differentiation-induction is performed by coculturing the nephron progenitor cell with embryonic spinal cord or a Wnt4-expressing cell.

(26) A distal renal tubular cell, characterized in that the cell is a cell population expressing E-cadherin, Brn1, and NCC, which was differentiation-induced from a nephron progenitor cell according to any one of (18) to (20).

(27) The distal renal tubular cell according to (26), wherein the differentiation-induction is performed by coculturing the nephron progenitor cell with embryonic spinal cord or a Wnt4-expressing cell.

(28) A podocyte, characterized in that the podocyte is a cell population expressing Wt1, Nephrin, and Podocin, which was differentiation-induced from a nephron progenitor cell according any one of (18) to (20).

(29) The podocyte according to (28), wherein the differentiation-induction is performed by coculturing the nephron progenitor cell with embryonic spinal cord or a Wnt4-expressing cell.

(30) A differentiation-inducing medium kit for inducing a pluripotent stem cell into a nephron progenitor cell, the kit comprising (i) a differentiation-inducing medium, and (ii) Wnt agonist, wherein at least three differentiation-inducing media comprising the Wnt agonist at a step-wise concentration are prepared before use, and wherein the step-wise concentration includes at least concentrations A, B and C, the concentrations being concentration A>concentration B>concentration C, and a concentration A is at least five times of a concentration C.

(31) The differentiation-inducing medium kit according to (30), wherein in the step-wise concentration of the Wnt agonist, the medium is prepared so that a concentration A is at least three times of a concentration B, and a concentration B is at least three times of a concentration C.

Advantageous Effect of Invention

According to the present invention, it has become possible to effectively induce the metanephric nephron progenitor cell from the stem cell (e.g. ES cell and iPS cell), and further, it has become possible to reconstruct the three-dimensional structure of the kidney including both of the glomerulus and the renal tubule. Thereby, there has been opened a possibility that using iPS cells which have been established from patients with a variety of diseases, disease-specific renal tubules and podocytes are made, and they can be applied to clarification of the disease state and development of novel drugs. Furthermore, from that this nephron progenitor cell formed the glomerulus accompanied with blood infiltration by transplanting into immunodeficiency mice, it is expected from now on that this leads to regeneration of the functional kidney having the urine producing ability.

BRIEF DESCRIPTION OF DRAWINGS

FIG. 14 is the results of comparison of the nephron progenitor cell marker gene expression in selected early stage renal progenitor cells. The relative expression level relative to a median which was standardized for every probe is shown as a log 2 ratio ($\log_2$ fold change). E8.5: selected Osr1-GFP-positive or negative cells from the embryonic body trunk. E9.5: selected Osr1-GFP-positive or negative cells from the embryonic body trunk. A GFP+ population was divided into an Itga8+/Pdgfra-population and others. E11.5MM: Osr1-GFP-positive or negative cells derived from the manually isolated metanephric mesenchyme. A GFP+ population was divided into an Itga8+/Pdgfra-population and others. Metanephric nephron progenitor cell marker genes, for example, Osr1, Wt1, Pax2, Six2, Gdnf and Crym were expressed in both of the Osr1+/Itga8+/Pdgfra−population at E9.5 and E11.5. On the other hand, a caudal Hox gene such as Hoxa10, a11, c10, d10, d11 and d12 was concentrated in the E11.5 metanephric mesenchyme.

DESCRIPTION OF EMBODIMENTS

Figure 1:
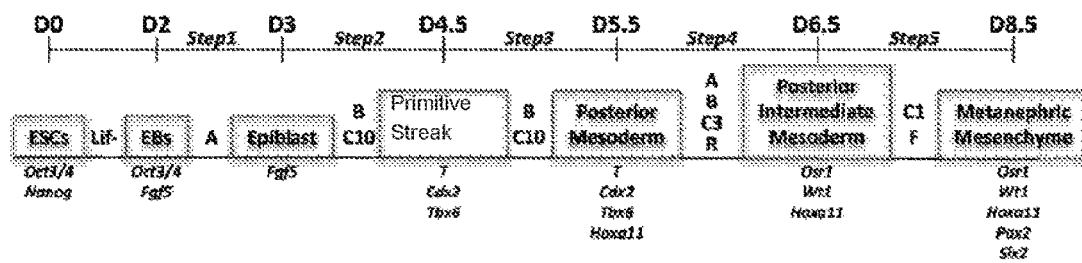
FIG. 1 shows an outline of a step of inducing the metanephric nephron progenitor cell (metanephric mesenchyme) from the mouse ES cell. A represents activin, B represents Bmp4, C represents CHIR99021, R represents retinoic acid, and F represents Fgf9. C10, C3, and C1 represent 10 µm, 3 µM, and 1 µM CHIR99021, respectively.

The present invention will be illustrated in detail below, but the present invention is not limited to aspects described below.

The inventors succeeded in inducing the metanephric nephron progenitor cell which can reconstruct the three-dimensional kidney including the renal tubule and the glomerulus, from mouse and human pluripotent stem cells. Since the renal tubule and the glomerulus are important two components for the renal function, the method of the present invention and the findings obtained using it are useful for elucidating the molecular mechanism underlying a human renal disease and, at the same time, can be utilized in regenerative medicine. The data shown in the present specification also verifies that a developmental process of the kidney is well conserved between a human and a mouse, and show robustness of the method of the present invention which faithfully reproduces a physiological process.

The previous researches have challenging the induction of the renal progenitor cell using a putative "lineage inducing factor", but they lacked a view point of how the metanephros, that is, the anlage of the adult kidney is posteriorized in the scheduled kidney region, that is, the intermediate mesoderm. It has previously been known that the ureteric bud which is one of two important elements constituting the metanephros is developed from the anterior intermediate mesoderm, and extended posteriorly. This time, we have newly revealed that a progenitor of the metanephric mesenchyme which is another constituent element is derived, not from the anterior intermediate mesoderm, but from the posterior undifferentiated mesoderm which was maintained in the transcription factor Brachyury (=T)-positive state until a term of termination of gastrulation, and posteriorized.

A transcription factor T which begins to be expressed at a stage of gastrulation initiation has previously been recognized as a "temporary" undifferentiated mesoderm marker, in research of the differentiation-induction from stem cells. However, recently, it has been shown that an undifferentiated progenitor cell population which has maintained the T-positive state exists at the posterior end of the embryo until termination of extension of the body trunk, and functions as a cell which is the origin of the caudal body trunk, that is, a "axial progenitor" (Non-Patent Literature 5: Takemoto et al., Nature 470, 394-398, 2011; Non-Patent Literature 6: Tzouanacou et al., Dev Cell 17, 365-376, 2009; Non-Patent Literature 7: Wilson et al., Development 136, 1591-1604, 2009). The data shown in the present specification suggests that this recently identified posterior part undifferentiated mesoderm (axial progenitor) would be the origin of the metanephric mesenchyme, that is, the nephron progenitor cell, and this is against the previous idea that the entire kidney is derived from the anterior intermediate mesoderm. Introduction of a model of the induction of axial progenitors can be further applied to the differentiation-induction of organs located at another caudal side.

As shown in Examples described below, the present inventors succeeded in posteriorization of a cell while it is maintained in the T-positive undifferentiated state, by utilizing Wnt agonist at a concentration higher than a concentration which is usually used for maintaining the undifferentiated state of mouse ES cells. Thereafter, by gradually decreasing a concentration of the Wnt agonist step-wisely, and further, adding the agonist in combination with a growth factor differentiation stage-specifically, the cell is differentiation-induced into the kidney lineage, and thus finally, formation of the metanephric nephron progenitor cell is enabled. Necessity of the Wnt agonist at a high concentration at an initial stage of the induction reflects that the Wnt signal is important for extending the caudal body trunk and maintaining axial progenitors in vivo. In a next step towards the posterior intermediate mesoderm, a reduction in a Wnt agonist concentration and addition of retinoic acid were effective, like a differentiation stage of the paraxial mesoderm, which forms the musculoskeletal of the body trunk. In addition, in this step, the syngeneic effect of activin on the gene induction of the kidney was also confirmed. Subsequently, in a step of differentiation from the posterior intermediate mesoderm to the metanephric mesenchyme, addition of Fgf9 and a further reduction in a Wnt signal are effective, and thereupon, addition of Bmp4, retinoic acid and activin is inhibitory, and it should be removed at this final step. This shows that each growth factor should be added stage-specifically.

These observation results may partially explain why the induction of the metanephric progenitor cell from an Osr1+ anterior intermediate mesoderm cell at E8.5 has previously failed. It is predicted that the Osr1+ anterior intermediate mesoderm cell which already exists at E8.5 does not contribute to the metanephros, and a T+/Osr1-population generates a genuine T-/Osr1+ posterior intermediate mesoderm cell having the ability to differentiate into the metanephros.

The "pluripotent stem cell" used in the present invention refers to a cell which has the self-replicating ability, can be cultured in vitro, and has the pluripotency to differentiate into a cell constituting an individual. Specifically, examples thereof include an embryonic stem cell (ES cell), an artificial pluripotent stem cell derived from a somatic cell (iPS cell) etc., and a cell which is particularly preferably used in the present invention is an iPS cell or an ES cell, particularly preferably a mouse iPS cell and a mouse ES cell, as well as a human iPS cell and a human ES cell.

The ES cell used in the present invention may be an ES cell derived from a mammal, and a kind thereof and a method of obtaining it are not particularly limited. Examples of the mammal include mouse, rat, guinea pig, hamster, rabbit, cat, dog, sheep, cow, horse, goat, monkey or human, preferably mouse or human.

The ES cell can be generally stablished finally as a cell strain, by culturing a fertilized egg in the blastocyst stage with feeder cells, dissociating proliferated cells derived from the internal cell mass, and further, repeating a passage operation.

In addition, the iPS cell (artificial pluripotent stem cell) is a cell which acquired the differentiation pluripotency, and is a cell which acquired the differentiation pluripotency equal to that of the ES cell, by introducing a few kinds of transcription factor (differentiation pluripotency factor) genes which confer the differentiation pluripotency to a somatic cell (e.g. fibroblast cell etc.). As the "differentiation pluripotency factor", many factors have been reported, and examples thereof are not particularly limited to, but include the Oct family (e.g. Oct3/4), the Sox family (e.g. Sox2, Sox1, Sox3, Sox15 and Sox17), the Klf family (e.g. Klf4, Klf2 etc.), the Myc family (e.g. c-Myc, N-Myc, L-Myc etc.), Nanog, LIN28 etc. Concerning a method of establishing the iPS cell, many have been already reported, and they can be referenced.

A method of culturing the ES cell derived from a mammal can be performed by the conventional method. For example, the cell can be maintained using medium to which leukemia inhibition factor (LIF), KSR (knock-out serum replacement), fetal bovine serum (FBS), nonessential amino acid, L-glutamine, pyruvic acid, penicillin, streptomycin, and β-mercaptoethanol have been added, for example, DMEM medium, using a mouse embryonic fibroblast cell (MEF cell) as a feeder cell.

Culturing of the iPS cell can be also performed by the conventional method. For example, the cell can be maintained using medium to which bFGF, KSR (knock-out serum replacement), nonessential amino acid, L-glutamine, penicillin, streptomycin, and β-mercaptoethanol have been added, for example, DMEM/F12 medium or Primate ES medium (Reprocell), using a mouse fibroblast cell as a feeder cell.

The differentiation-induction of the nephron progenitor cell from the pluripotent stem cell in the present invention, for example, the ES cell or the iPS cell includes both of the culture system containing feeder cells, and the feeder-free culture system. As medium used in differentiation-induction, medium which is generally used can be used, and the medium is not particularly limited as far as the object of the present invention can be attained, but can be prepared using medium which is used for culturing an animal cell as basal medium. Examples of the basal medium include BME medium, BGjB medium, CMRL 1066 medium, Glasgow MEM medium, modified MEM medium, IMDM medium, Medium 199 medium, Eagles MEM medium, αMEM medium, DMEM medium, Ham's medium, RPMI 1640 medium, Fischer's medium, Dulbecco's medium, modified Dulbecco's medium, and mixed media thereof. For example, preferably, in the differentiation-induction of the ES cell, mixed medium of Iscove's modified Dulbecco's medium and Ham's F12 can be used, and in the differentiation-induction of the iPS cell, DMEM/F12 medium can be used, being not limiting.

The medium used in the culturing method of the present invention can be serum-containing medium, or serum-free medium, and from a view point of security of safety of cell transplantation by exclusion of heterogeneous components, serum-free medium is preferable. Herein, the serum-free medium means medium not containing non-adjusted or unpurified serum, and medium in which purified blood-derived components or animal tissue-derived components (e.g. growth factor) or serum replacement are mixed, falls under the serum-free medium. Examples of such serum-free medium are not limited to, but include serum-free medium to which a suitable amount (e.g. 1-20%) of commercially available KSR has been added, serum-free medium to which insulin and transferrin have been added, medium to which factors derived from cells have been added, etc.

The differentiation-induction of the nephron progenitor cell from the pluripotent stem cell can be performed using medium in which respective components and factors have been added to the aforementioned medium, in each step, according to the present invention, as described in detail later. The component and the factor to be added to the medium are not limited to, but examples thereof include B27, N2, Insulin-transferrin-serenium, β-mercaptoethanol, ascorbic acid, and Non-essential amino acid.

The "differentiation" or the "differentiation-induction" of the pluripotent stem cell mentioned in the present invention is used in a sense that it includes the differentiation-induction from the pluripotent stem cell to the intermediate mesoderm, further, to the metanephric nephron progenitor cell, further, or alternatively, is also used in a sense that it includes the differentiation-induction of them into the three-dimensional kidney including the renal tubule and the glomerulus.

Figure 2:
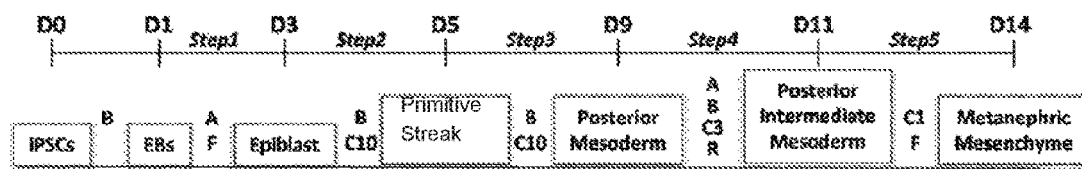
FIG. 2 shows an outline of a step of inducing the metanephric nephron progenitor cell (metanephric mesenchyme) from the human iPS cell. A represents activin, B represents Bmp4, C represents CHIR99021, R represents retinoic acid, and F represents Fgf9.

One aspect of the present invention is a method of differentiation-inducing a nephron progenitor cell from a pluripotent stem cell derived from a mammal. An outline of an entire step of inducing the nephron progenitor cell from the ES cell using the present invention is shown in FIG. 1, and an outline of an entire step of inducing the nephron progenitor cell from the iPS cell is shown in FIG. 2.

When the nephron progenitor cell is differentiation-induced from the pluripotent stem cell derived from a mammal using the present invention, it is necessary that the method includes the following three steps (a) to (c) in that order: step (a), a step of culturing an embryoid body which has been derived from the pluripotent stem cell in medium containing Bmp, and Wnt agonist at a high concentration (concentration A); step (b), a step of culturing the embryoid body in medium containing Bmp, and Wnt agonist at an intermediate concentration (concentration B); and step (c), a step of culturing the embryoid body in medium containing Fgf, and Wnt agonist at a low concentration (concentration C).

Bmp used in the steps (a) and (b) is selected from the group consisting of the Bmp family such as Bmp1, Bmp2, Bmp4, Bmp6, Bmp7, Bmp8a, Bmp8b and Bmp10, is preferably selected from Bmp2, Bmp4 or Bmp7, and is further preferably Bmp4.

Fgf used in the step (c) is selected from the Fgf family such as Fgf2, 9, 20 etc., preferably, is selected from Fgf2, Fgf9 or Fgf20, and is more preferably Fgf9.

A concentration of the Wnt agonist used in the steps (a) to (c) is concentration A>concentration B>concentration C, and a concentration A is at least five times of a concentration C.

The method of the present invention includes these steps in an order of (a), (b), and (c), if necessary, another step may be included between respective steps, and preferably, the method includes (a), (b) and (c) continuously. By continuation of these steps, the nephron progenitor cell can be effectively differentiation-induced from the pluripotent stem cell.

In the differentiation-inducing method of the present invention, preferably, in the step (b), the medium further comprises activin, more preferably, activin and retinoic acid.

In the differentiation-inducing method of the present invention, particularly preferably, in the step (c), the medium is medium containing none of Bmp, activin or retinoic acid.

The posterior mesoderm is induced by the step (a), the posterior intermediate mesoderm is induced by the step (b), and the metanephric nephron progenitor cell (metanephric mesenchyme) is induced by the step (c).

The embryoid body used in the step (a) can be prepared by culturing the pluripotent stem cell (e.g. ES cell or iPS cell) in arbitrary medium, preferably serum-free medium. For example, when the mouse pluripotent stem cell is used, the embryoid body is prepared using preferably mouse ES cells without any limitation, further preferably, the embryoid body which was treated with activin before treatment of the step (a) to transiently induce the expression of Fgf5 is used. Examples of the concentration of activin in the medium include 0.1 to 3 ng/mL, preferably 0.5 to 1 ng/mL. Treatment with activin can be performed, for example, for 1 to 2 days, preferably for 1 day. Thereupon, when Bmp4 is used together at around 0.1 ng/mL to 0.3 ng/mL, a differentiation-induction efficiency is increased in some cases, depending on the cell strain.

On the other hand, when the human pluripotent stem cell is used, preferably, the embryoid body is prepared using cells obtained by treating human iPS cells with Bmp4 and a Rock inhibitor (Y27632) (if necessary, by further adding Fgf) without any limitation, further preferably, the embryoid body obtained by then treating the embryoid body with activin and Fgf is used. Examples of the concentration of Bmp4 in the medium include 0.3 to 5 ng/mL, preferably 0.5 to 2 ng/mL, examples of the concentration of the Rock inhibitor (Y27632) in the medium include 1 to 100 ng/mL, preferably 5 to 20 ng/mL, examples of the concentration of Fgf in the medium include 0 to 20 ng/mL, and examples of the concentration of activin in the medium include 0.1 to 5 ng/mL, preferably 0.5 to 1 ng/mL. Treatment with Bmp4 and the Rock inhibitor (Y27632), Fgf is performed, for example, for 1 to 2 days, preferably for 1 day, and treatment with activin and Fgf can be performed, for example, for 1 to 4 days, preferably for 2 days.

In the differentiation-inducing method of the present invention, it is important that in the steps (a), (b) and (c), the concentrations A, B and C of the Wnt agonist contained in the medium used in each step have a specific relationship. A concentration of the Wnt agonist in the medium used in each step is concentration A>concentration B>concentration C, and a concentration A is at least five times of a concentration C, preferably, a concentration A is at least two times of a concentration B, and a concentration B is at least two times of a concentration C, further preferably, a concentration A is at least three times of a concentration B, and a concentration B is at least three times of a concentration C. A concentration C of the Wnt agonist in the step (c) is not particularly limited as far as the differentiation-induction occurs in the method of the present invention, and is appropriately selected depending on the Wnt agonist used, and for example, when CHIR99021 is used, examples of the concentration C include 0.1 to 3.0 µM, preferably 0.5 to 2.0 µM.

For example, when CHIR99021 is used, examples of a combination of the concentrations A and C of the Wnt agonist in the steps (a) and (c) are not limited to, but include a combination in which a concentration A is selected from 6 to 20 μM, preferably 7 to 15 μM, more preferably 10 μM, and a concentration C is selected from 0.5 to 2 μM, preferably 0.7 to 1.5 μM, more preferably 1 μM. In addition, for example, when CHIR99021 is used, examples of a combination of the concentrations A, B and C of the Wnt agonist in the steps (a), (b) and (c) are not limited to, but include a combination in which a concentration A is selected from 6 to 20 μM, preferably 7 to 15 μM, more preferably 10 μM, a concentration B is selected from 2 to 6 μM, preferably 2 to 4.5 μM, more preferably 3 μM, and a concentration C is selected from 0.5 to 2 μM, preferably 0.7 to 1.5 μM, more preferably 1 μM.

The Wnt agonist which can be used in the present invention is not particularly limited, as far as it has the Wnt agonist activity. The Wnt agonist is defined as a drug which activates TCF/LEF-mediated transcription in cells. Therefore, the Wnt agonist is selected from genuine Wnt agonist which binds to Frizzled receptor family members including all of Wnt family proteins to activate them, an intracellular β-catenin degradation inhibitor and a substance which activates TCF/LEF. The Wnt agonist mentioned in the present invention refers to agonist which stimulates the Wnt activity in cells, by at least 10%, preferably at least 30%, more preferably at least 50%, further preferably at least 70%, still further preferably at least 90%, most preferably 100%, as compared with the level of the Wnt activity in the absence of this molecule. As is known to a person skilled in the art, the Wnt activity can be examined by measuring the transcription activity of Wnt, with pTOPFLASH and pFOPFLASH Tcf luciferase reporter constructs (Korinek et al., Science 275: 1784-1787, 1997).

The Wnt agonist which can be used in the present invention includes a secretory glycoprotein including Wnt-1/Int-1; Wnt-2/Irp (Int-1-associated protein); Wnt-2b/13, Wnt-3/Int-4; Wnt-3a; Wnt-4; Wnt-5a; Wnt-5b; Wnt-6; Wnt-7a; Wnt-7b, Wnt-8a/8d; Wnt-8b; Wnt-9a/14; Wnt-9b/14b/15; Wnt-10a; Wnt-10b/12; Wnt-11 and Wnt-16. Furthermore, the Wnt agonist includes the R-spondin family of a secretory protein, and Norrin being a secretion-controlling protein which functions like the Wnt agonist in a point that it binds to a Frizzled-4 receptor with high affinity, and induces activation of a Wnt signaling pathway. A small molecule agonist of the Wnt signaling pathway, and an aminopyrimidine derivative are also clearly included as the Wnt agonist.

The Wnt agonist included in the definition also includes a Wnt signaling pathway inhibitory substance, a GSK-3 inhibitor, a Dkk1 antagonist etc. The GSK-3 inhibitor includes a GSK-α or β inhibitor, is defined as a substance which inhibits the kinase activity of a GSK-3α or β protein, for example, the ability to phosphorylate β catenin, and many substances are known. Specific examples thereof include CHIR99021 (6-[[2-[[4-(2,4-dichlorophenyl)-5-(4-methyl-1H-imidazol-2-yl)-2-pyrimidinyl]amino]ethyl]amino]nicotinonitrile), lithium, valproic acid, Kenpaullone (9-bromo-7,12-dihydroindolo[3,2-d][1]benzazepine-6(5H)-one) and Alsterpaullone (9-nitro-7,12-dihydroindolo[3,2-d][1]benzazepine-6(5H)-one) of the benzazepinone family, 5-chloro-indirubin, indirubin-3'-monooxime and BIO (another name, GSK-3β inhibiter IX; 6-bromoindirubin-3'-oxime) which are an indirubin derivative, SB216763 (3-(2,4-dichlorophenyl)-4-(1-methyl-1H-indol-3-yl)-1H-pyrrole-2,5-dione) and SB415286 (3-[(3-chloro-4-hydroxyphenyl)amino]-4-(2-nitrophenyl)-1H-pyrrole-2,5-dione) which are a maleimide derivative, TDZD-8 (another name, GSK-3β inhibiter I; 4-benzyl-2-methyl-1,2,4-thiadiazolidine-3,5-dione) and OTDZT (another name, GSK-3β inhibiter III; 2,4-dibenzyl-5-oxothiadiazolidine-3-thione) which are a thiadiazolidinone (TDZD) analogue, GSK-3β inhibitor VII (4-dibromoacetophenone) which is a phenyl a bromo methyl ketone compound, L808-mts (another name, GSK-3β peptide inhibitor; Myr-N-GKEAPPAPPQSpP-NH$_2$) which is a cell membrane permeable phosphorylation peptide etc.

The Wnt agonist which can be used in the present invention further includes a Wnt signaling pathway inhibitory substance, and a substance which is known as the Wnt signaling pathway inhibitory substance, or commercially available can be used.

The Wnt agonist which can be used in the present invention includes both of natural agonist and synthetic agonist, as far as they are included in the definition, and may be any of a protein, a high molecule, and a small molecule. Examples of the Wnt agonist which can be used in the present invention are not limited to, but include preferably a GSK-3 inhibitor, more preferably CHIR99021, BIO, or SB415286, particularly preferably CHIR99021. A use concentration of each Wnt agonist can be appropriately selected in conformity with the intended use, and for example, a concentration which can exert the same effect as the effect obtained in the case of using CHIR99021 can be selected.

As Bmp which is used in the step (a), any of the aforementioned Bmp(s) can be used, and a use concentration of each Bmp compound can be appropriately selected in conformity with the intended use. For example, when Bmp4 is used, Bmp4 from any source can be used, Bmp is preferably human Bmp4, a concentration of Bmp4 in the medium is not particularly limited as far as the effect of the differentiation-induction is obtained, but examples thereof include 0.1 to 3 ng/mL, preferably 0.3 to 1.5 ng/mL. In addition, when another Bmp compound is used, a concentration which can exert the same effect as the effect obtained in the case of using Bmp4 can be appropriately selected.

As Bmp used in the step (b), any of the aforementioned Bmp(s) can be used, and a use concentration of each Bmp compound can be appropriately selected in conformity with the intended use. For example, when Bmp4 is used, Bmp4 from any source can be used, and Bmp4 is preferably human Bmp4. A concentration of Bmp4 in the medium is not particularly limited as far as the effect of the differentiation-induction is obtained, but examples thereof include 0.1 to 30 ng/mL, preferably 1 to 10 ng/mL. In addition, when another Bmp compound is used, a concentration which can exert the same effect as the effect obtained in the case of using of Bmp4 can be appropriately selected.

In a preferable aspect, as activin used in the step (b), activin from any source can be used, and activin is preferably human activin A. In addition, a concentration of activin in the medium is not particularly limited as far as the effect of the differentiation-induction is obtained, but examples thereof include 2.5 to 40 ng/mL, preferably 7.5 to 15 ng/mL.

In addition, in another preferable aspect, a concentration of retinoic acid used in the step (b) in the medium is not particularly limited as far as the effect of the differentiation-induction is obtained, but examples thereof include 0.001 to 1 preferably 0.01 to 0.3 μM.

As Fgf used in the step (c), any of the aforementioned Fgf(s) can be used, and a use concentration of each Fgf compound can be appropriately selected in conformity with the intended use. For example, when Fgf9 is used, Fgf from any source can be used, and Fgf9 is preferably human Fgf9. A concentration thereof in the medium is not particularly limited as far as the effect of the differentiation-induction is obtained, but examples thereof include 1 to 25 ng/mL preferably 2.5 to 10 ng/mL. In addition, when another Fgf compound is used, a concentration which can exert the same effect as the effect obtained in the case of using Fgf9 can be appropriately selected.

The number of days for treatment in the steps (a), (b) and (c) is not particularly limited as far as the nephron progenitor cell can be induced, and there is the following preferable number of days, for each of a mouse and a human.

When the nephron progenitor cell is induced using mouse pluripotent stem cells, in culturing, the step (a) can be performed, for example, for 1 day to 4 days, preferably for 2 days to 3 days, particularly preferably for 2.5 days, the step (b) can be performed preferably for 0.5 day to 2 days, particularly preferably for 1 day, and the step (c) can be performed, for example, for 0.5 to 3 days, preferably for 1 day to 2.5 days, particularly preferably for 2 days.

On the other hand, when the nephron progenitor cell is induced using human pluripotent stem cells, in culturing, the step (a) is performed, for example, for 3 days to 11 days, preferably for 4 days to 10 days, particularly preferably for 6 days, the step (b) is performed preferably for 1 day to 3 days, particularly preferably for 2 days, and the step (c) is performed, for example, for 1 to 5 days, preferably for 2 days to 4 days, particularly preferably for 3 days.

Another aspect of the present invention is a metanephric nephron progenitor cell which was induced by the differentiation-inducing method of the present invention. The nephron progenitor cell which was induced by the method of the present of invention is characterized in that it is a cell population expressing all of transcription factors, Osr1, Wt1, Pax2, Six2, Hoxa10, and Hoxa11 defining the metanephric mesenchyme, and those genes are coexpressed at the single cell level at a high probability. The nephron progenitor cell of the present invention is a metanephric nephron progenitor cell which can reconstruct the three-dimensional kidney including not only the renal tubule but also the glomerulus.

Another aspect of the present invention is a proximal renal tubule cell, a distal renal tubule cell, and a podocyte, which were further differentiation-induced from the metanephric nephron progenitor cell of the present invention. The characteristic of the proximal renal tubule cell is a cell population of cells expressing Cadherin6, Megalin, and LTL. The characteristic of the distal renal tubule cell is a cell population of cells expressing E-cadherin, Brn1, and NCC. The characteristic of the glomerulus cell is a cell population of cells expressing Wt1, Nephrin, and Podocin. The proximal renal tubule cell, the distal renal tubule cell, or the podocyte can be obtained, for example, by coculturing a nephron progenitor cell with embryonic spinal cord or a Wnt4-expressing cell, being not limiting.

In addition, sorting of each constituent cell after coculturing is not particularly limited, but for example, each cell-specific membrane protein (e.g. podocalyxin in the case of podocyte, Cadherin6 in the case of proximal renal tubule, Ecadherin in the case of distal renal tubule) is antibody-stained after cell dissociation treatment using trypsin etc., and each constituent cell can be sorted using FACS (flow cytometer).

Another aspect of the present invention is a method of making a three-dimensional kidney in which the renal tubule and the glomerulus are reconstructed, using the nephron progenitor cell obtained by the method of the present invention. The method of making the three-dimensional kidney using the nephron progenitor cell obtained by the method of the present invention can be performed, for example, by coculturing the nephron progenitor cell with embryonic spinal cord or a Wnt4-expressing cell at an air-liquid interface. The condition of coculturing can be performed by referring to the method described in Kispert et al., Development 125, 4225-4234, 1998 (Non-Patent Literature 8), but the condition is not limited thereto, and includes the condition which was appropriately changed or improved by a person skilled in the art based on other known findings. The thus made kidney forms the structure of the three-dimensional kidney including the renal tubule and the glomerulus.

Another aspect of the present invention is a three-dimensional kidney in which the renal tubule and the glomerulus are reconstructed, the kidney being made by using the nephron progenitor cell obtained by the method of the present invention. The method of making the three-dimensional kidney is as described above.

Another aspect of the present invention is medium for inducing a nephron progenitor cell form a pluripotent stem cell, and a medium kit. One characteristic of the medium of the present invention is a combination of media comprising Wnt agonists having the step-wisely changed concentrations, and the present invention is also a medium kit for making such a combination of media. Examples thereof include a medium kit consisting of inducing medium for inducing the nephron progenitor cell or the kidney from the pluripotent stem cell, and Wnt agonist, and the kit can be used by adding the Wnt agonist to the medium so that a concentration becomes step-wise before use. The medium kit of the present invention can further comprise any one or more of Bmp4, activin, and retinoic acid.

As described above, the present invention has enabled the induction of the metanephric nephron progenitor cell from the pluripotent stem cell. The metanephric nephron progenitor cell made by the method of the present invention can contribute to construction of further matured nephron components, and it becomes possible to confer the physiological function of the kidney by binding them with the structure derived from the ureteric bud.

EXAMPLES

Hereinafter, the present invention will be described in further detail with reference to the Examples. However, the present invention is not limited thereto.

(A) Material and Method (1) Generation of Mutant Mice

GFP was inserted into the AgeI site of exon 2, such that the N-terminal 12 amino acids of Osr1 were fused in-frame to GFP. The 5' HpaI-AgeI Osr1 genomic fragment (2.8 kb) fused to EGFP, as well as the 3' BamHI-BamHI fragment (5.5 kb), were incorporated into a vector containing Neo flanked by loxP sites and DTA in tandem, as reported previously (Takasato et al., 2004). The targeting vector was electroporated into E14.1 ES cells, and three of 480 G418-resistant clones were correctly targeted as determined by Southern blotting analyses using 5' probes after BamHI digestion. The correctly targeted ES clones were used to generate germline chimeras that were bred with C57BL/6J female mice. When Neo was deleted by crossing the Osr1-GFP mutant mice with mice expressing Cre ubiquitously, the phenotypes and EGFP expression patterns were identical to those of the original mutant mice. Genotyping of the offspring was performed by PCR using a forward primer, 5'-TATGTTGAGGGGGCAGTAGGTTC-3', and two reverse primers, 5'-GTTGGGCAGGTGGTCCGAGGGCA-3' and 5'-TAGGTCAGGGTGGTCACGAGGGT-3', producing products of 320 bp for the wild-type allele and 420 bp for the mutant allele. T$^{nEGFP\text{-}CreERT2/+}$ (Acc. No. CDB0604K: http://www.cdb.riken.jp/arg/mutant%20mice%20list.html), Wt1$^{tm1(EGFP/cre)Wtp}$ mice, Six2$^{tm3(EGFP/cre/ERT2)Amc}$ mice and Gt(ROSA)26Sor$^{tm9(CAG\text{-}tdTomato)Hze}$ mice were purchased from Jackson Laboratory. All animal experiments were performed in accordance with institutional guidelines and ethics review committees.

(2) In Vitro Colony-Formation Assay

In vitro colony-formation assays were performed as described previously (Osafune et al., 2006). Briefly, progenitor cells were sorted by a FACS Aria II (Becton Dickinson) and plated onto NIH3T3 cells stably expressing Wnt4 at a low density (1,250-10,000 cells/well of 6-well plates). The cells were then cultured in DMEM/F12 containing 5% knockout serum replacement (Invitrogen), 10 µg/ml insulin, 6.7 µg/1 sodium selenite, 5.5 µg/ml transferrin, $1\times10^{-7}$ mol/l dexamethasone, 10 mmol/l nicotinamide, 2 mmol/l L-glutamine, 50 µmol/l 2-mercaptoethanol, 5 mmol/l HEPES and penicillin/streptomycin.

(3) Immunostaining

Specimens were fixed in 10% formalin, embedded in paraffin and cut into 6-µm sections. Immunostaining was carried out automatically using a BlueMap or DABmap kit and an automated Discovery System (Roche) or manually for immunofluorescence staining. For fluorescence immunohistochemistry, paraffin-embedded sections were deparaffinized and autoclaved at 121° C. for 5 min in citrate buffer (pH 6.0). After incubation in blocking solution for 1 h at room temperature, the sections were incubated overnight with primary antibodies at 4° C., followed by incubation with secondary antibodies conjugated with Alexa Fluor 488, 561, 594, 633 or 647. Nuclei were counter-stained with DAPI (Roche). For frozen sections, samples were fixed with 4% paraformaldehyde, embedded in optimal cutting temperature (OCT) compound (Tissue Tek) and cryosectioned at 10-µm thickness. For immunostaining, the OCT compound was removed by three washes with PBS, and the sections were incubated in blocking solution. The subsequent procedure was the same as that for paraffin section staining.

(4) Sorted Embryonic Cell Culture

For embryonic tissue cultures at E8.5, the presomitic regions of 6-10 somite-stage embryos were harvested and T-GFP+ cells were sorted by FACS. The sorted cells were aggregated at 7,000 cells per aggregate in 96-well low-cell-binding plates and cultured in serum-free chemically-defined medium. In the embryonic tissue cultures at E9.5, the posterior regions from the 23rd somite region of 22-26 somite-stage embryos were harvested and Osr1-GFP+ or Wt1-GFP+ cells were sorted by FACS. The sorted cells were aggregated at 10,000 cells per aggregate in 96-well low-cell-binding plates and cultured in serum-free chemically-defined medium.

(5) Mouse ES Cell and Human iPS Cell Culture

Mouse ES cells (Osr1-GFP) were maintained on murine embryonic fibroblasts in DMEM (Invitrogen) supplemented with 15% fetal calf serum, 0.1 mM 2-mercaptoethanol (Nacalai Tesque) and 1,000 U/ml leukemia inhibitory factor (ESGRO). EB3-DsRed cells, gifts from Dr. Hitoshi Niwa (CDB RIKEN), were maintained as reported previously (Usui et al., Am. J. Pathol. 180, 2417-2426, 2012). Before the initiation of differentiation, the ES cells were passaged once onto feeder cell-free gelatin-coated dishes in DMEM (Invitrogen) supplemented with 15% fetal bovine serum, 0.1 mM 2-mercaptoethanol, 1,000 U/ml leukemia inhibitory factor, 3 µM CHIR99021 (Wako) and 1 µM PD0325901 (Wako). ES cell differentiation was carried out in serum-free medium as follows. The ES cells were dissociated with Accutase (ESGRO) and cultured in serum-free differentiation medium comprising 75% Iscove's modified Dulbecco's medium (Invitrogen) and 25% Ham's F12 medium (Invitrogen) supplemented with 0.5×N2 and 0.5×B27 (without retinoic acid) supplements (Invitrogen), 0.5× penicillin/streptomycin, 0.05% bovine serum albumin, 2 mM glutamine (Invitrogen), 0.5 mM ascorbic acid (Sigma) and 4.5× $10^{-4}$ M 1-thioglycerol. Harvested cells were aggregated at 1,000 cells per aggregate in 96-well low-cell-binding plates to form embryoid body (EBs). After 48 h (on day 2), the EBs were dissociated with Accutase and re-aggregated in serum-free differentiation medium with addition of 0.5 ng/ml human activin A (R&D Systems). After 24 h (on day 3), the medium was switched to BC10 medium containing 1 ng/ml human Bmp4 (R&D Systems) and 10 µM CHIR99021. After 36 h (on day 4.5), the medium was refreshed with new medium (BC10). On day 5.5, the medium was changed to ABC3R medium containing 10 ng/ml activin, 3 ng/ml Bmp4, 3 µM CHIR99021 and 0.1 µM retinoic acid. On day 6.5, the medium was changed to C1F medium containing 1 µM CHIR99021 and 5 ng/ml human Fgf9 (R&D Systems).

Human iPS cells (201B7) were maintained on murine embryonic fibroblasts in Primate ES medium (ReproCELL) supplemented with 5 ng/ml recombinant human basic Fgf (WAKO). On the 3rd day of culture, iPS cell colonies were detached and harvested in 1 mg/ml of Type 4 collagenase (Invitrogen). In order to remove murine embryonic fibroblasts, suspended cells harvested stood for 10 min so that only iPS cell colonies were collected. The iPS cell differentiation was carried out in serum-free medium as follows. The iPS cells were dissociated with Accutase (ESGRO) and cultured in serum-free differentiation medium comprising DMEM/F12 (Invitrogen) supplemented with 2% (vol/vol) B27 (without retinoic acid), 2 mM L-glutamine, 1% (vol/vol) ITS, 1% (vol/vol) nonessential amino acids (without retinoic acid), 90 µM β-mercaptoethanol and 0.5× penicillin/streptomycin. Harvested cells were aggregated at 10,000 cells per aggregate in 96-well low-cell-binding plates to form EBs, in the presence of 10 µM Y27632 (Wako), and 0.5 ng/ml human Bmp4 (R&D Systems). After 24 h (on day 1), the medium was changed to mesoderm-inducing medium containing 1 ng/ml human activin A and 20 ng/ml human basic Fgf (R&D Systems). After 48 h (on day 3), the medium was switched to BC10 medium containing 1 ng/ml human Bmp4 (R&D Systems) and 10 µM CHIR99021. Subsequently, half of the culture medium volume was refreshed with new medium (BC10) every other day. On day 9, the medium was changed to ABC3R medium containing 10 ng/ml activin, 3 ng/ml Bmp4, 3 µM CHIR99021 and 0.1 µM retinoic acid. On day 11, the medium was changed to C1F medium containing 1 µM CHIR99021 and 5 ng/ml human Fgf9 (R&D Systems). All data shown are representative examples of at least three independent experiments, unless indicated otherwise.

(6) Organ Culture of Metanephric Mesenchyme or Induced Metanephric Progenitors

The mouse embryo metanephric mesenchyme cells or induced ES cell aggregates were cultured with embryonic spinal cord taken from E11.5 or E12.5 embryos or on 3T3Wnt4 cells at the air-fluid interface on a polycarbonate filter (0.8 µm; Whatman) supplied with DMEM containing 10% fetal calf serum, as described previously (Non-Patent Literature 8: Kispert et al., Development 125, 4225-4234, 1998; Non-Patent Literature 4: Osafune et al., Development 133, 151-161, 2006).

(7) Flow Cytometry Analysis with Immunostaining

Induced cell aggregates from embryonic tissues or ES cells were dissociated by incubation with 0.25% trypsin for 5 min. After blocking in normal mouse serum (Thermo Scientific), cell surface marker staining was carried out in buffer comprising 1% bovine serum albumin, 1×HBSS and 0.035% $NaHCO_3$. Data were analyzed with FlowJo software (Treestar).

(8) Antibodies

The antibodies used were as follows: rabbit anti-Pax2 (Covance; 1:800); fluorescein anti-LTL (FL-1321; Vector Laboratories; 1:100); chicken anti-GFP (Abcam; 1:1000); rabbit anti-GFP (Invitrogen; 1:400); rabbit anti-Itga8 (Sigma; 1:200); rabbit anti-Pdgfra (Cell Signaling Technology; 1:500); mouse anti-Pdgfra (Takakura et al., J. Histochem Cytochem 45, 883-893, 1997) (1:500); rabbit anti-Wt1 (Santa Cruz Biotechnology; 1:200); mouse anti-Wt1 (Dako; 1:100); rabbit anti-Six2 (Proteintech; 1:500); mouse anti-Sall1 (PPMX Perseus Proteomics; 1:200); mouse anti-E-cadherin (BD Biosciences; 1:800); rabbit anti-Cdh6 (gift from Dr. Dressler (Cho et al., Development 125, 803-812, 1998); 1:400); mouse anti-Aqp1 (Abcam; 1:100); rabbit anti-Podocin (gift from Dr. Asanuma (Lydia et al., Am J Nephrol 35, 58-68, 2012); 1:400); guinea-pig anti-Nephrin (Progen; 1:200); rabbit anti CD31 (Abcam, 1:25); rat anti CD34 (Abcam 1:100); rabbit anti DsRed (Clontech 1:100).

(9) Quantitative RT-PCR

RNA was isolated using an RNeasy Plus Micro Kit (Qiagen), and then reverse-transcribed with random primers and Superscript III (Invitrogen). Quantitative PCR was carried out using a Real-Time PCR System (Applied Biosystems) and Thunderbird SYBR qPCR Mix (Toyobo). All samples were normalized by the β-actin expression using the relative standard curve method.

(10) Microarray Analysis

The following seven types of specimens were compared: Osr1-GFP-positive and -negative cells of E8.5 embryos; Osr1-GFP+/Itga8+/Pdgfra− population, Osr1-GFP+ except for Itga8+/Pdgfra− population and Osr1-GFP-negative population of the caudal body trunk of E9.5 embryos; Osr1-GFP+/Itga8+/Pdgfra− population and Osr1-GFP+ except for Itga8+/Pdgfra− population of the manually dissected metanephric mesenchyme at E11.5. Microarray analyses were performed using an Agilent SurePrint G3 mouse gene expression (8×60K) microarray. The data were normalized by GeneSpring GX software (Agilent). The microarray data have been deposited in the National Center for Biotechnology Information Gene Expression Omnibus (GSE).

B. Examples

Example 1: The Osr1+/Integrina8+/Pdgfra− Population Representing Colony-Forming Nephron Progenitors The metanephric mesenchyme gives rise to the epithelia of glomeruli (including podocytes) and renal tubules, which constitute the major parts of the nephrons, as shown by cell fate analyses involving labeling of mesenchyme expressing the transcription factor Six2. The inventors previously proved the presence of nephron progenitors by establishing a novel colony-formation assay. When dissociated metanephric mesenchymal cells, which strongly express Sall1, were plated onto feeder cells stably expressing Wnt4, single cells formed colonies that expressed glomerular and renal tubule markers (Non-Patent Literature 9: Nishinakamura et al., 2001; Non-Patent Literature 4: Osafune et al., 2006). Therefore, the Sall1-high and Six2-positive metanephric mesenchyme represents a nephron progenitor population in the embryonic kidney.

Figure 3:
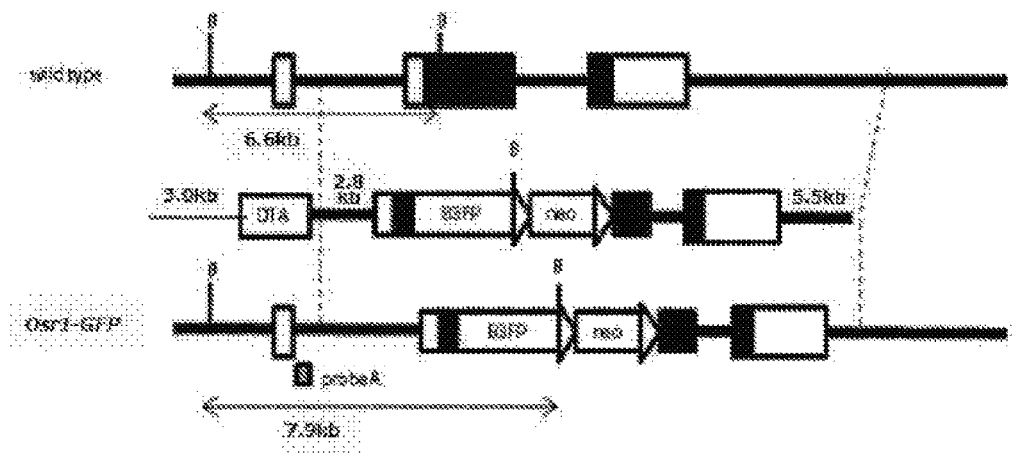
FIG. 3 shows target strategy for making an Osr1-GFP knock-in mouse. EGFP was introduced into an Osr1 gene locus so that an N-terminal amino acid of Osr1 binds to EGFP. B represents BamHI.
Figure 4:
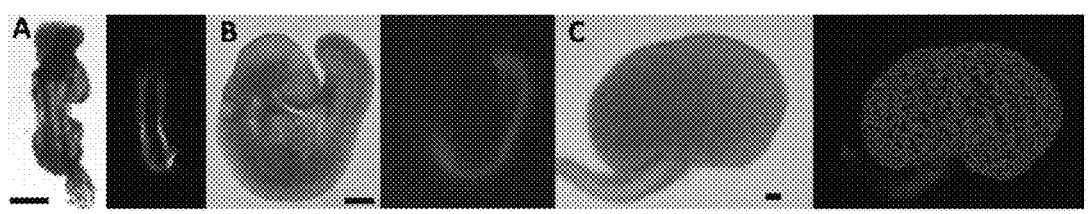
FIG. 4 shows EGFP expression at E8.5 (A), E9.5 (B) and E15.5 (C) of the Osr1-GFP knock-in mouse. A scale bar is 500 μm.

Osr1 is another metanephric mesenchyme marker and also one of the earliest markers for the intermediate mesoderm, and is thus continuously expressed in the renal precursor population throughout kidney development (Non-Patent Literature 10: James et al., Development 133, 2995-3004, 2006; Non-Patent Literature 1: Mugford et al., 2008b). Osr1-GFP knock-in mice were generated (FIG. 3) and it was confirmed that green fluorescent protein (GFP) was expressed in the intermediate mesoderm at E8.5-E9.5 and the metanephric mesenchyme at E11.5-E15.5 (FIGS. 4A-C).

Next, it was evaluated that the Osr1-GFP-positive population contained colony-forming nephron progenitors as follows. The caudal parts of E8.5 embryos (posterior from the heart level) and E9.5 embryos (posterior from the forelimb level) were harvested. For the E11.5 and E15.5 experiments, embryonic metanephroi were manually dissected. After dissociation of the harvested cells, Osr1+ cells were sorted by FACS and seeded onto Wnt4 feeder cells. At day 8, the numbers of colonies were counted. The results are shown in Table 1. As shown in the following, similar to the previous reports of the inventors, the Osr1-GFP-positive population sorted from E11.5 and E15.5 embryonic kidneys contained colony-forming nephron progenitors.

TABLE 1

|  | E8.5 | E9.5 | E11.5 | E15.5 |
| --- | --- | --- | --- | --- |
| tissue source | caudal half of the embryo | caudal half of the embryo | metanephric mesenchyme | whole kidney |
| Osr1-GFP positive cells (%) | 31.9 ± 2.9 | 31.5 ± 6.3 | 97.9 ± 0.78 | 26.7 ± 1.9 |
| Colony formation in Osr1-GFP+ cells (%) | 0 | 0.037 ± 0.013 | 9.1 ± 0.48 | 23.3 ± 2.8 |

Figure 5:
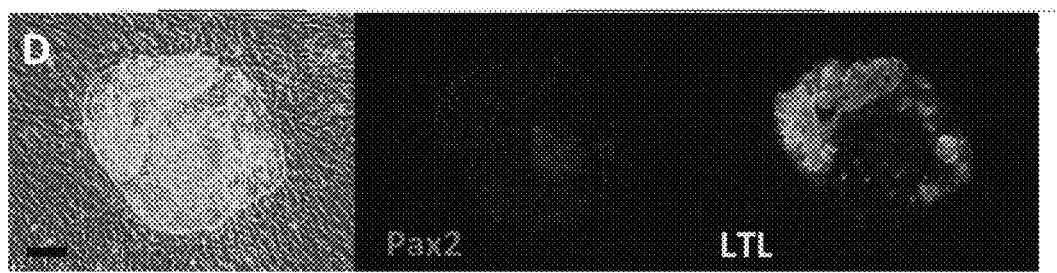
FIG. 5 shows a bright-field image (left), Pax2 expression (central), and LTL expression (right) of colonies which were formed by an Osr1-GFP-positive population. A scale bar is 100 μm.
Figure 6:
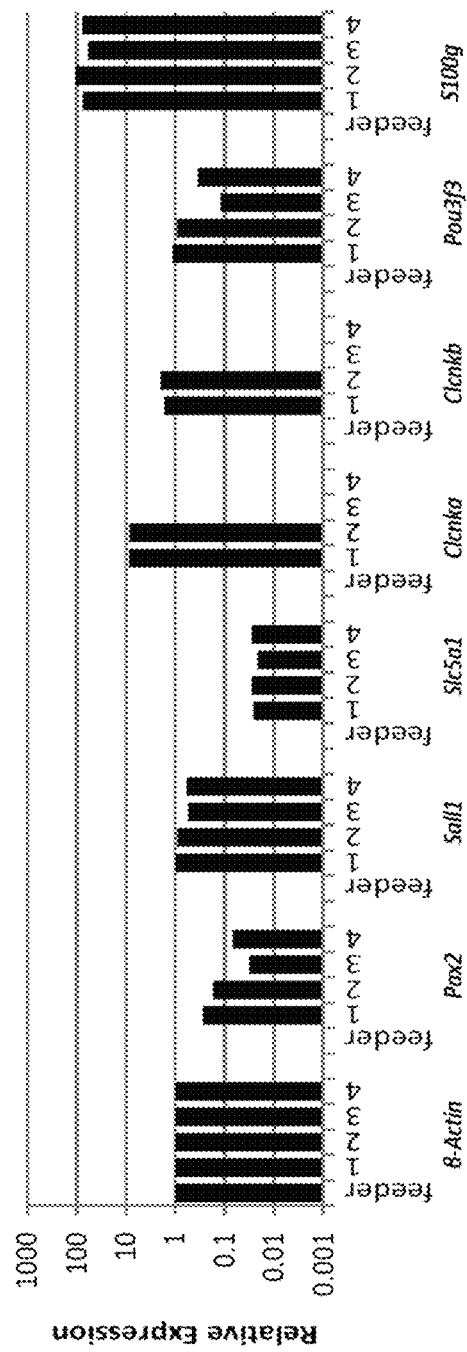
FIG. 6 shows expression of a kidney-associated gene of a colony which was formed by the Osr1-GFP-positive population, as the relative expression relative to β-actin. Each first lane shows only Wnt4 feeder cells not containing the colony. A marker is a kidney lineage marker: Pax2 and Sall1; proximal renal tubule marker: Slc5a1; Henle' loop marker: Clcnka and Clcnkb; distal renal tubule marker: Pou3f3; connecting tubule marker: s100g, respectively.

The expression of nephric translation factors and markers for differentiated renal tubules in the colonies was evaluated (FIGS. 5 and 6). As a result, the colonies expressed nephric transcription factors, such as Pax2 and Sall1, as well as markers for differentiated renal tubules. Therefore, the Osr1+ metanephric mesenchyme contains colony-forming nephron progenitors.

Figure 7:
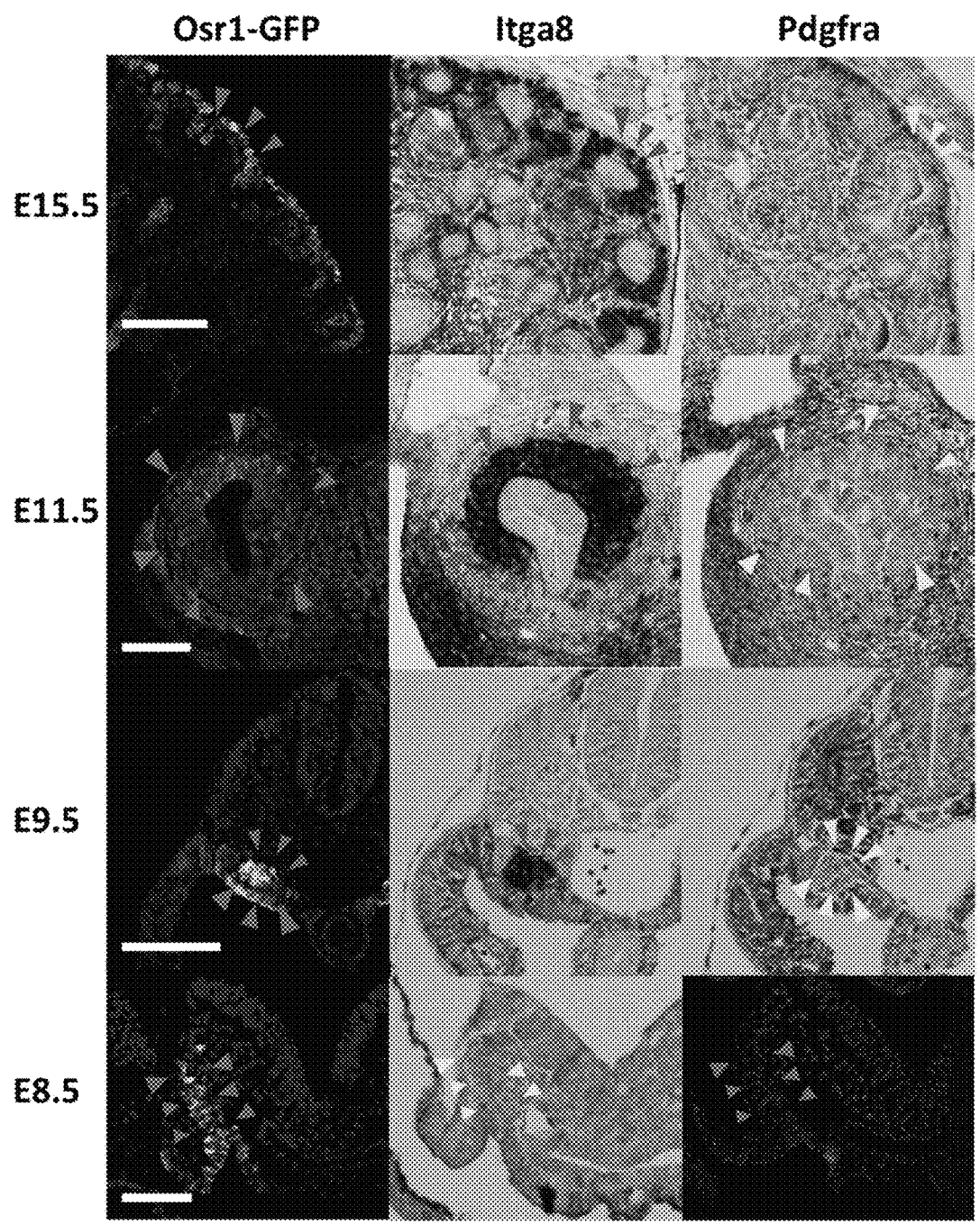
FIG. 7 shows expression of Itga8 and Pdgfra at E8.5, E9.5, E11.5 and E15.5 of the Osr1-GFP knock-in mouse, by immunostaining of an embryonic section. An arrowhead shows the capping mesenchyme at E15.5 and E11.5, the aggregated intermediate mesoderm at E9.5, and the intermediate mesoderm at E8.5, respectively. A scale bar is 100 μm.
Figure 8:
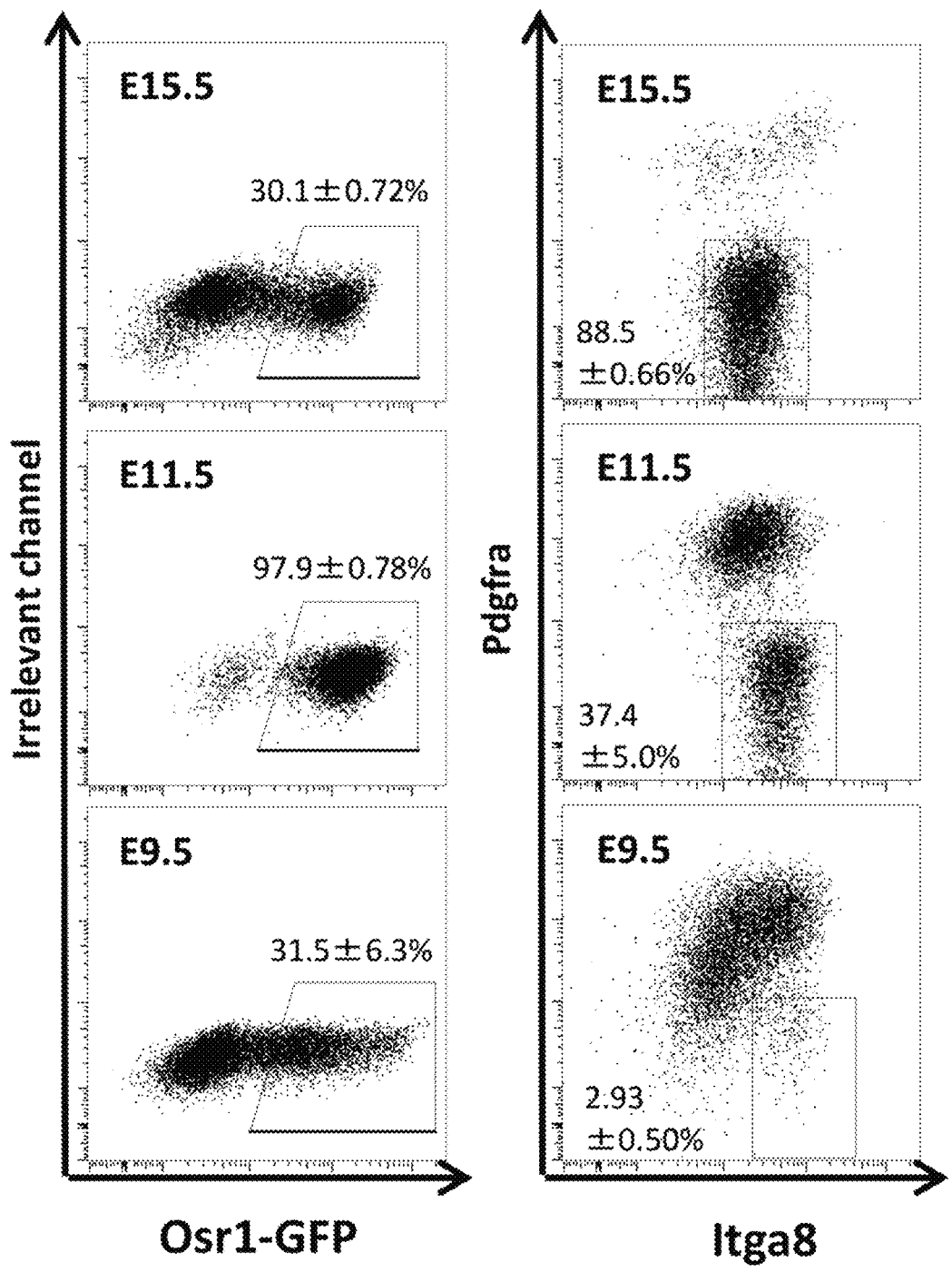
FIG. 8 shows the results of FACS analysis of Osr1-GFP (left) and Itga8/Pdgfra (right), of an embryo at each developmental stage.

Next, cell surface markers that can further enrich the nephron progenitors were serached. At E15.5 and E11.5, Integrina8 (Itga8) was strongly expressed in the capping mesenchyme around the ureteric bud tips, while Pdgfra was excluded from the population (FIG. 7). By fluorescence-activated cell sorting (FACS) analyses, the existence of Itga8+/Pdgfra− fractions in the Osr1-GFP+ populations of E15.5 and E11.5 embryonic kidneys was identified (FIG. 8). The existence of enriched colony-forming nephron progenitors in Osr1-GFP+/Inga8+/Pdgfra− cell population is evaluated as follows. E9.5 or E11.5 specimens were harvested. For the E10.5 experiments, the mesonephric region (from anterior forelimb end to anterior hindlimb end) or metanephric region (from anterior hindlimb end to posterior hindlimb end) was dissected manually. The harvested tissues were dissociated and immunostained with anti-Itga8 and anti-Pdgfra antibodies. Osr1+/Itga8+/Pdgfra− cells were sorted by FACS and seeded onto Wnt4 feeder cells. At day 8, the numbers of colonies were counted. The results are shown in Table 2 below. As shown in the following, colony-forming nephron progenitors were enriched in the Osr1+/Itga8+/Pdgfra− fractions.

TABLE 2

|  | E9.5 (caudal trunk) | E10.5 (meso-nephric region) | E10.5 (meta-nephric region) | E11.5 (meta-nephric mesenchyme) |
| --- | --- | --- | --- | --- |
| GFP+ population(%) | 31.5 ± 6.3 | 22.2 ± 3.1 | 31.5 ± 2.8 | 97.9 ± 0.78 |
| Itga8+/Pdgfra− population in GFP+ population(%) | 2.93 ± 0.50 | 2.85 ± 1.4 | 3.45 ± 1.3 | 37.4 ± 5.0 |
| Colony forming ratio (%) | 1.10 ± 0.26 | 1.47 ± 0.20 | 30.9 ± 1.5 | 50.9 ± 5.2 |

Figure 9:
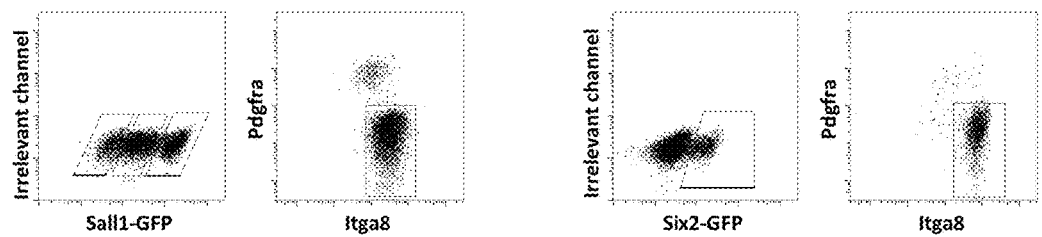
FIG. 9 shows a population having high Sall1-GFP (left) and a Six2-GFP-positive population (right) in the E11.5 metanephros of the Osr1-GFP knock-in mouse, and the results of FACS analysis of the Itga8/Pdgfra expression.

The reliability of these cell surface markers was confirmed using GFP knock-in mice for Sall1 and Six2. The result is shown in FIG. 9. Most of the Sall1-GFPhigh or Six2-GFP+ cells were Itga8+/Pdgfra−. Therefore, it was shown that the Itga8+/Pdgfra− fraction represented the colony-forming nephron progenitors.

Example 2: The Anterior Intermediate Mesoderm at E9.5 Containing Colony-Forming Progenitors that Contribute to the Mesonephros Next, the expressions of nephron progenitor markers and the colony-forming abilities of Osr1-GFP-positive cells at earlier stages were examined. As shown in FIG. 5 and Table 1, at E8.5, any overlap of GFP with Itga8 was not detected and no colonies were formed by the GFP+ population. At E9.5, colony formation by the GFP+ population was delected (0.037±0.013%).

The colony-forming cells were enriched by finding a GFP+ region that was Itga8+/Pdgfra− (FIG. 5), and sorting of the Osr1+/Itga8+/Pdgfra− population (1.10±0.26%, FIG. 6; Table 2). However, even after the enrichment, the colony-forming frequency was significantly lower than those of the Osr1+/Itga8+/Pdgfra− populations from the metanephric region at E10.5 and E11.5 (30.9±1.5% and 50.9±5.2%, respectively; Table 2). In contrast, the colony-forming frequency of the Osr1+/Itga8+/Pdgfra− population from the mesonephric region at E10.5 (1.47±0.20%) was as low as that from E9.5. Since the mesonephros, which is located anterior to the metanephros, develops earlier than the metanephros and forms much fewer nephrons, it was hypothesized that the colony-forming cells at E9.5 may represent mesonephric nephron progenitors.

Figure 10:
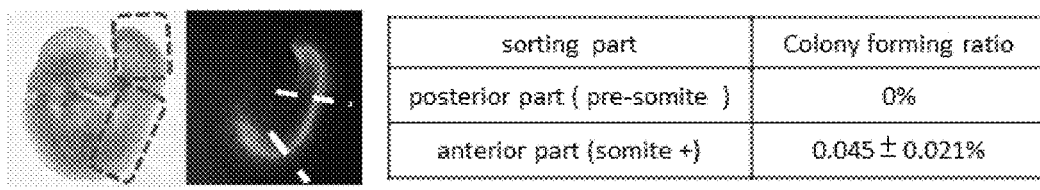
In FIG. 10, the anterior part (somite level 7~22) and the posterior part (posterior to smite level 23) of an embryo were manually isolated, and 20,000 Osr1+ cells were seeded on Wnt signal feeder cells. A colony formation ratio of each part is shown on a right side as the mean±s.e.m. (n=3).
Figure 11:
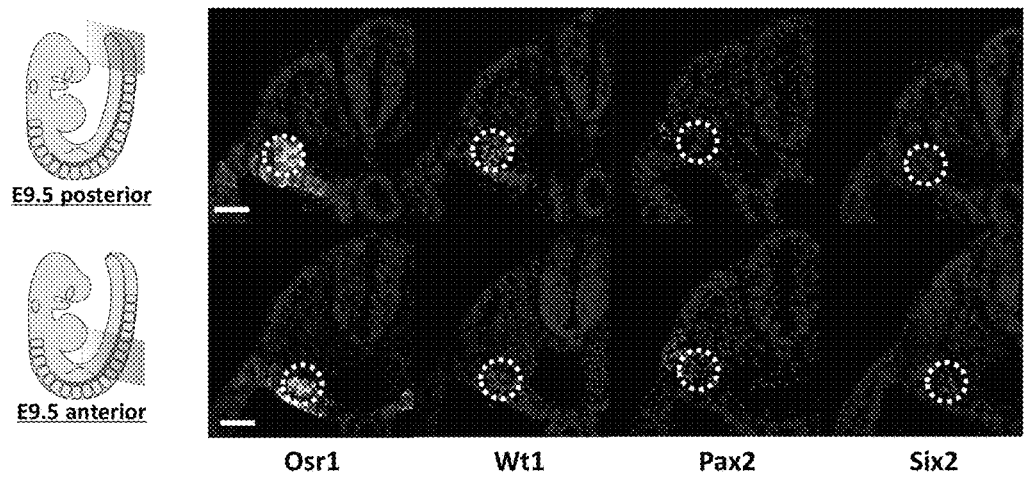
In FIG. 11, various markers of the nephron progenitor cell in the intermediate mesoderm at E9.5 were confirmed by immunostaining. A contour of the intermediate mesoderm was drawn with a dashed line. A scale bar is 50 μm.
Figure 12:
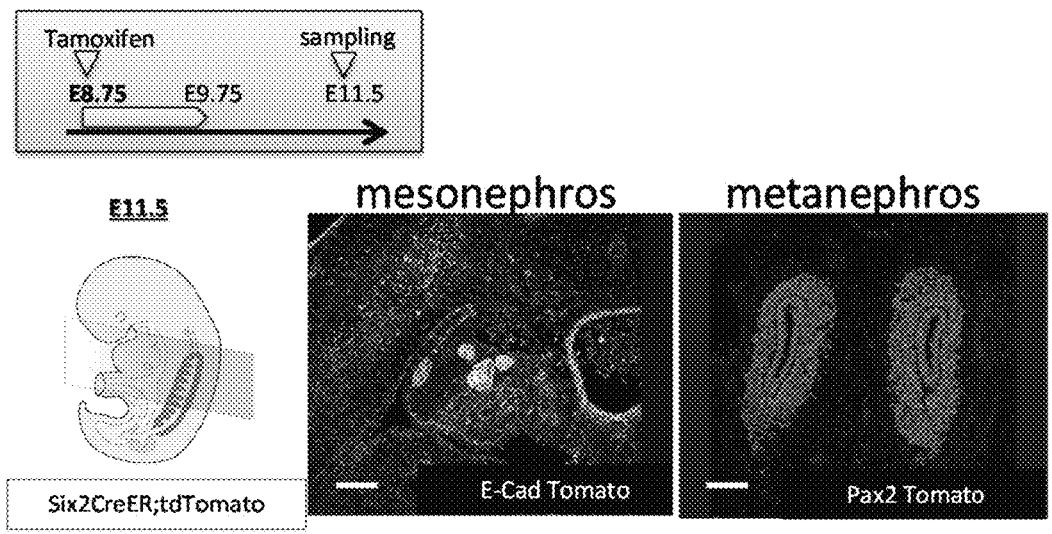
In FIG. 12, a Six2-GFPCreER mouse and a mouse having a tdTomato reporter gene were crossed, and tamoxifen was injected at E8.75 to temporarily activate Cre at around E9.5. An embryo was collected at E11.5, and immunostained with E-cadherin (green) or Pax2 (green). tdTomato-positive red cells were detected in the mesonephros, but not detected in the metanephros. A scale bar is 100 μm.

Colony-forming progenitors were, as shown in FIG. 10, only detected among the anterior part of GFP+ cells in the E9.5 embryo. As shown in FIG. 11, Pax2 and Six2, which mark nephron progenitors, were predominantly expressed in the anterior part of the intermediate mesoderm, while Wt1, another nephron progenitor marker, was expressed in both the anterior and posterior parts. These data suggest molecular differences between the anterior and posterior intermediate mesoderm at E9.5. Furthermore, Six2-GFPCreER mice were crossed with mice carrying a tdTomato reporter allele, and injected tamoxifen to transiently activate Cre at E9.5. When analyzed at E11.5, as shown in FIG. 12, labeled cells were detected in the mesonephros, but not in the metanephros. Therefore, the mesonephric nephron progenitors that exist in the anterior part may not give rise to the metanephric nephron progenitors that are located posteriorly.

Example 3: Metanephric Nephron Progenitor Induction from the Posterior Intermediate Mesoderm at E9.5

Figure 13:
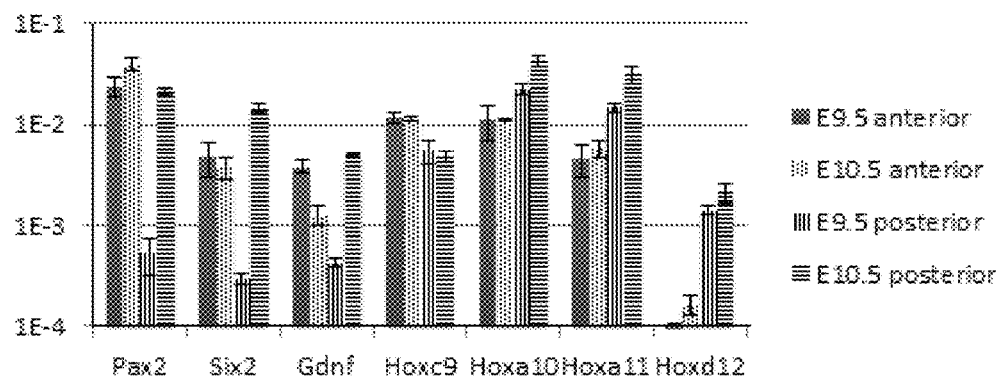
FIG. 13 shows the expression of each transcript in the intermediate mesoderm at E9.5 and E10.5. E9.5 anterior and E10.5 anterior: mesonephric progenitor cell, E10.5 posterior: metanephric progenitor cell, E9.5 posterior: posterior intermediate mesoderm. The relative expression of each transcript relative to the β-actin expression is shown by the mean±s.e.m. (n=3).
Figure 15:
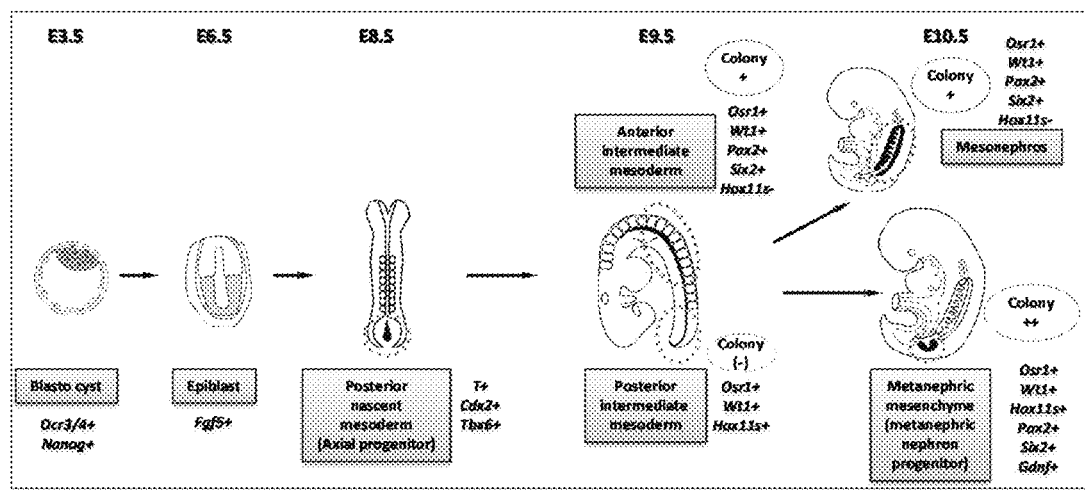
FIG. 15 is a schematic view of development of the mouse kidney. The T+/Cdx2+/Tbx6+ posterior undifferentiated mesoderm at E8.5 generates the metanephric mesenchyme via the posterior intermediate mesoderm. The intermediate mesoderm located anterior to E9.5, which expresses Pax2 and Six2, and does not express Hox11s, generates the mesonephros, and forms some colonies on Wnt4 feeder cells. The intermediate mesoderm located posterior to E9.5, which does not express Pax2 and Six2 or does not form a colony, expresses a caudal Hox gene. The metanephric mesenchyme located posterior to E10.5 expresses a caudal Hox gene, Pax2 and Six2, and forms many colonies on Wnt4 feeder cells.

Microarray and quantitative PCR analyses were performed using the Osr1+/Itga8+/Pdgfra− colony-forming presumptive mesonephric progenitors at E9.5 and metanephric nephron progenitors at E10.5-E11.5. Results are shown in FIGS. 13 and 14. While both types of progenitors expressed many transcriptional factors in common, such as Osr1, Wt1,Pax2 and Six2, as well as Gdnf (a cytokine essential for kidney development), the metanephric progenitors expressed posterior Hox genes including Hoxa10, Hoxa11 and Hoxd12 more abundantly. The Hox11 family genes, which start to be expressed at the posterior end of the embryo around E9.0, are essential for metanephros development by dictating the metanephric region along the anterior-posterior axis in the intermediate mesoderm. Furthermore, a cell fate mapping study showed that the Osr1+ intermediate mesoderm at E9.5 contributes to the metanephric mesenchyme. Therefore, it was hypothesized that the non-colony-forming Osr1+/posterior Hox+ intermediate mesoderm, which was located posteriorly at E9.5, could be a precursor population of the metanephric nephron progenitors (FIG. 15, FIG. 11 and FIG. 13). Notably, the expression levels of Pax2, Six2 and Gdnf in this posterior intermediate mesoderm at E9.5 were still much lower than those in the posterior metanephric progenitors at E10.5, indicating that they were distinct (FIG. 13).

Figure 16:
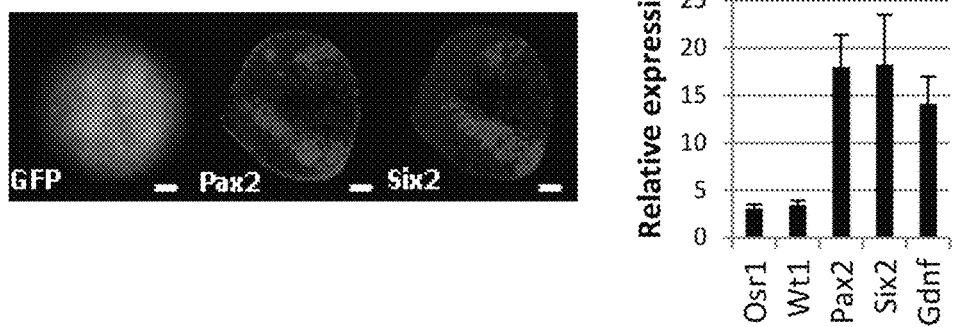
FIG. 16 is the results of GFP fluorescence and immunostaining of cultured cell aggregates, when Osr1-GFP+ cells which were selected from the posterior part of an E9.5 embryo were cultured in the presence of Y27632 (left) and the results of the relative expression of each transcript relative to the time of culturing initiation (mean±s.e.m., n=3, right).
Figure 17:
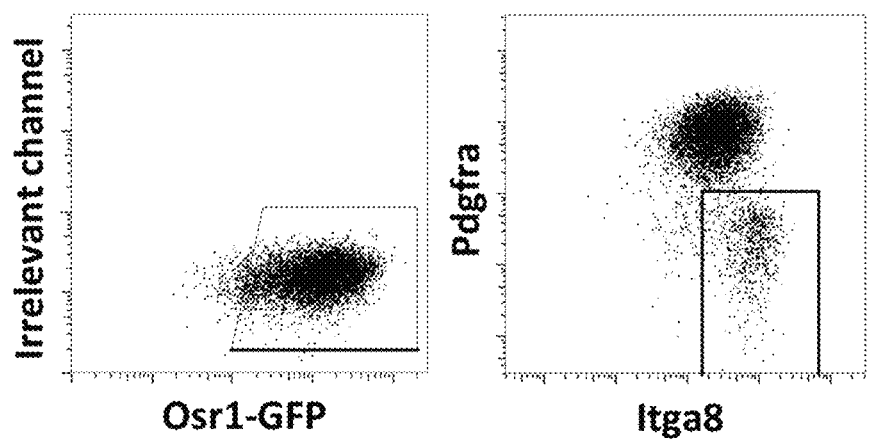
FIG. 17 is the results of FACS analysis of the Osr1-GFP expression (left) and the Itga8/Pdgfra expression (right) of the cultured cell aggregates.
Figures 18, 19:
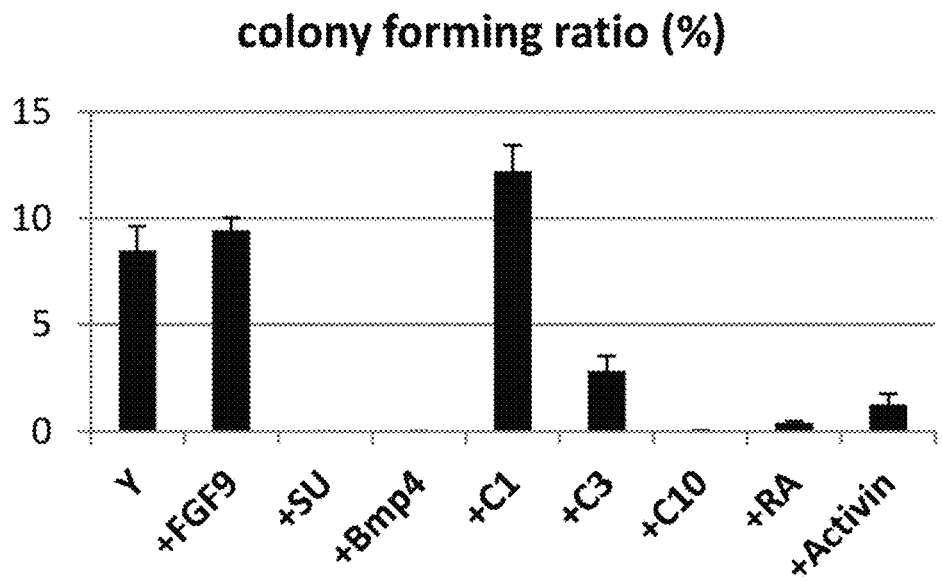
FIG. 18 is the results showing a colony formation ratio of the cultured cell aggregates (n=3). Y: Y27632 (Rock inhibitor); SU: SU5402 (Fgfr1 inhibitor); C1: 1 μM CHIR99021 (canonical Wnt agonist); C3: 3 μM CHIR99021, C10: 10 μM CHIR99021; RA: retinoic acid.
FIG. 19 is the results of comparison of the expressions of Fgf, Bmp, and Wnt-associated genes in selected early stage kidney progenitor cells, by microarray analysis. The relative expression of each probe relative to a standardized mean value is expressed as a log 2 ratio ($\log_2$ fold change).

To test the hypothesis, Osr1-GFP+ cells from the caudal part of E9.5 embryos were sorted, and were plated into low-cell-binding plates in the presence of the Rho kinase inhibitor Y27632, which supports cell survival. The results are shown in FIG. 16. The cells spontaneously re-aggregated and formed spheres within 24 h. At 48 h of culture, the aggregates retained intense GFP signals and showed more than 10-fold higher expressions of Pax2, Six2 and Gdnf compared with the starting point. FACS analyses (FIG. 17) also showed the emergence of an Osr1+/Itga8+/Pdgfra− population (10.0±0.01% of the total cells). When these aggregates were dissociated and stimulated with Wnt4, colony formation was observed as shown in FIG. 18. The results suggested in vitro derivation of metanephric nephron progenitors from the posterior intermediate mesoderm.

Figure 20:
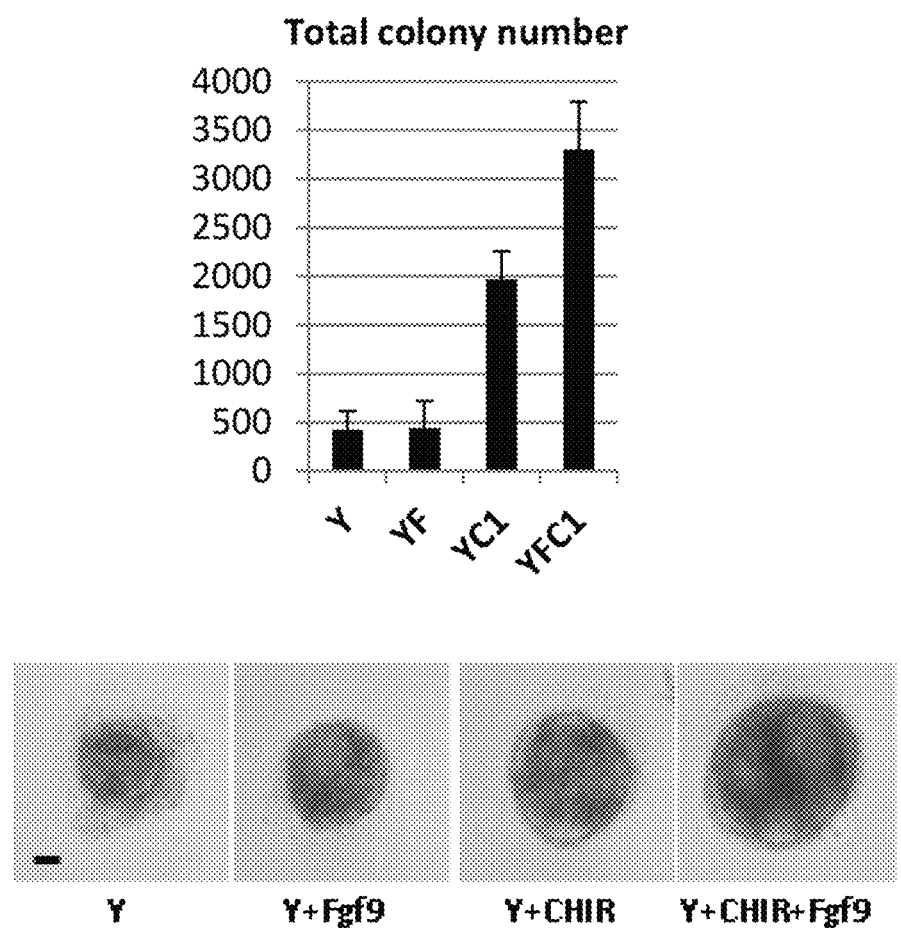
FIG. 20 shows influence on colony formation by addition of Fg19 and a low concentration of Wnt agonist. Y: Y27632 (Rock inhibitor); F: Fgf9; C1: 1 CHIR99021.
Figure 21:
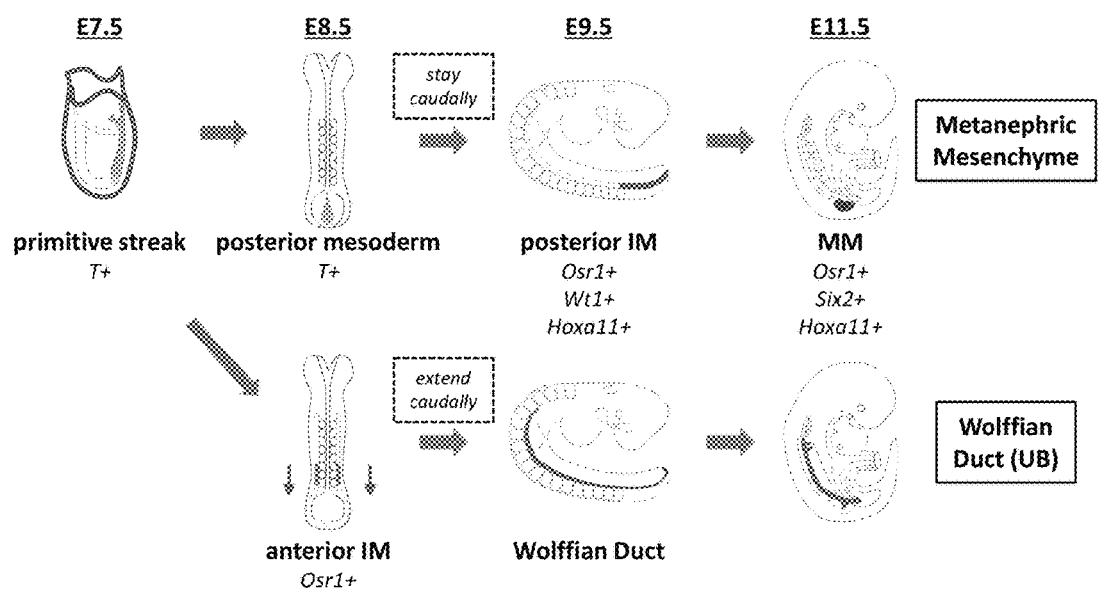
FIG. 21 shows a line separation model of the ureteric bud and the metanephric mesenchyme from the mesoderm.

The effects of growth factors in this process were addressed. From the microarray data and quantitative PCR analysis, it was shown that the accumulated expressions of Fgf ligands (especially Fgf9 and Fgf20), receptors and their downstream target genes in the colony-forming populations at both E9.5 and E11.5, while the Bmp and Wnt targets were down-regulated (FIG. 19). As shown in FIG. 18, inhibition of Fgf signaling, exogenous addition of Bmp4 or high concentrations of a Wnt agonist (3 or 10 μM CHIR99021; CHIR), as well as addition of retinoic acid or activin, were inhibitory for the induction of colony-forming progenitors and nephric gene expressions, whereas addition of FGF9 or a low concentration of the Wnt agonist (1 μM CHIR) slightly improved the colony formation. Since Osr1-GFP is expressed by a rather broad population, including the lateral plate mesoderm, the efficacy of these factors was examined using Wt1-GFP knock-in mice. The Wt1-GFP knock-in mice show more restricted expression in a region of the intermediate mesoderm (FIG. 11). As shown in FIG. 20, addition of Fgf9 and a low dose of the Wnt agonist synergistically promoted sphere growth, and increased colony formation by the spheres.

Thus, the combination of 1 μM CHIR and Fgf9 (C1F) was optimal for induction of metanephric nephron progenitors from the posterior intermediate mesoderm. These observations are consistent with previous findings showing requirements of Fgf receptors and Fgf9/Fgf20 for the formation and maintenance of the metanephric mesenchyme, respectively (Non-Patent Literature 11: Barak et al., Dev Cell 22, 1191-1207, 2012; and Non-Patent Literature 12: Poladia et al., Dev Biol 291, 325-339, 2006).

Example 4: The Precursor of the Metanephric Mesenchyme being Maintained in the T-Positive Caudal Population Until the E8.5 Post-Gastrulation Stage Next, the inventors searched for an in vitro method to differentiate the mesoderm at earlier stages into metanephric mesenchyme by way of the E9.5 posterior intermediate mesoderm. One report has shown that both the metanephric mesenchyme and ureteric bud derive from the intermediate mesoderm, which appears around embryonic day (E) 8.5 and expresses the transcription factor Osr1 (Non-Patent Literature 1: Mugford et al., Dev Biol 324, 88-98, 2008). Several other reports have shown that the ureteric bud originates from the anterior intermediate mesoderm, and its anlage, the Wolffian duct elongates in an anterior-to-posterior manner, as demonstrated by direct labeling in chick embryos (Non-Patent Literature 13: Atsuta et al., Dev Growth Differ 55, 579-590, 2013; Non-Patent Literature 14: Attia et al., Development 139, 4143-4151, 2012; Non-Patent Literature 15: Obara-Ishihara et al., Development 126, 1103-1108, 1999; Non-Patent Literature 16: Saxen, Organogenesis of the Kidney (New York: Cambridge University Press) (1987)). In murine embryos, the Pax2/8-positive anterior intermediate mesoderm at E8.5, called the pronephric anlage, is supposed to be the equivalent population, and is included in the Osr1-positive region. Thus, the effects of many combinations of growth factors on sorted E8.5 Osr1-GFP+ cells were initially examined. However, it was unable to induce colony-forming progenitors.

Therefore, the inventors tried an alternative approach. Deletion of T (Brachyury), a representative marker of the primitive streak and posterior nascent mesoderm, causes a caudal truncation that includes the metanephric region (Non-Patent Literature 17: Herrmann et al., Nature 343, 617-622, 1990). $T^{nEGFP-CreERT2/+}$ mice was crossed with mice carrying the tdTomato reporter allele, and tamoxifen was injected at the gastrulation stage (E6.5 and E7.5), when the initial germ layer formation takes place. When analyzed at E11.5, most of the mesodermal tissues, including the heart, limbs and kidneys, were labeled. Next, tamoxifen was injected at E8.5, and it found that labeled cells were only detected in the lower trunk of the E11.5 embryo, including the metanephric mesenchyme located at the hindlimb level. On the other hand, the heart and forelimbs, which are anteriorly located mesodermal tissues, were no longer labeled. Importantly, when sections were created at the metanephric level, only the metanephric mesenchyme, and not the ureteric bud, was labeled. These findings indicate that the origin of the ureteric bud has already become segregated at E8.5, which is consistent with the notion that the ureteric bud originates from the anterior intermediate mesoderm at E8.5 and elongates caudally. However, when tamoxifen was injected at E9.5, only the tail region was labeled, and no labeled cells were observed in the metanephric mesenchyme region.

Taken together, the precursor of the metanephric mesenchyme is maintained and posteriorized in the T-positive state until the E8.5 post-gastrulation stage. Presumably, this could in part correspond to the "axial progenitor", which was recently recognized as the source of the caudal body trunk. These data also reveal differences in the developmental processes between the posteriorly located metanephric mesenchyme and the anteriorly located mesodermal tissues, such as the heart, which have been successfully induced from pluripotent stem cells by way of the T-positive state in the initial short period of differentiation (Non-Patent Literature 18: Burridge et al., Cell Stem Cell 10, 16-28, 2012).

Example 5: Metanephric Mesenchyme Induction from the T-Positive Caudal Precursor at E8.5

Figure 22:
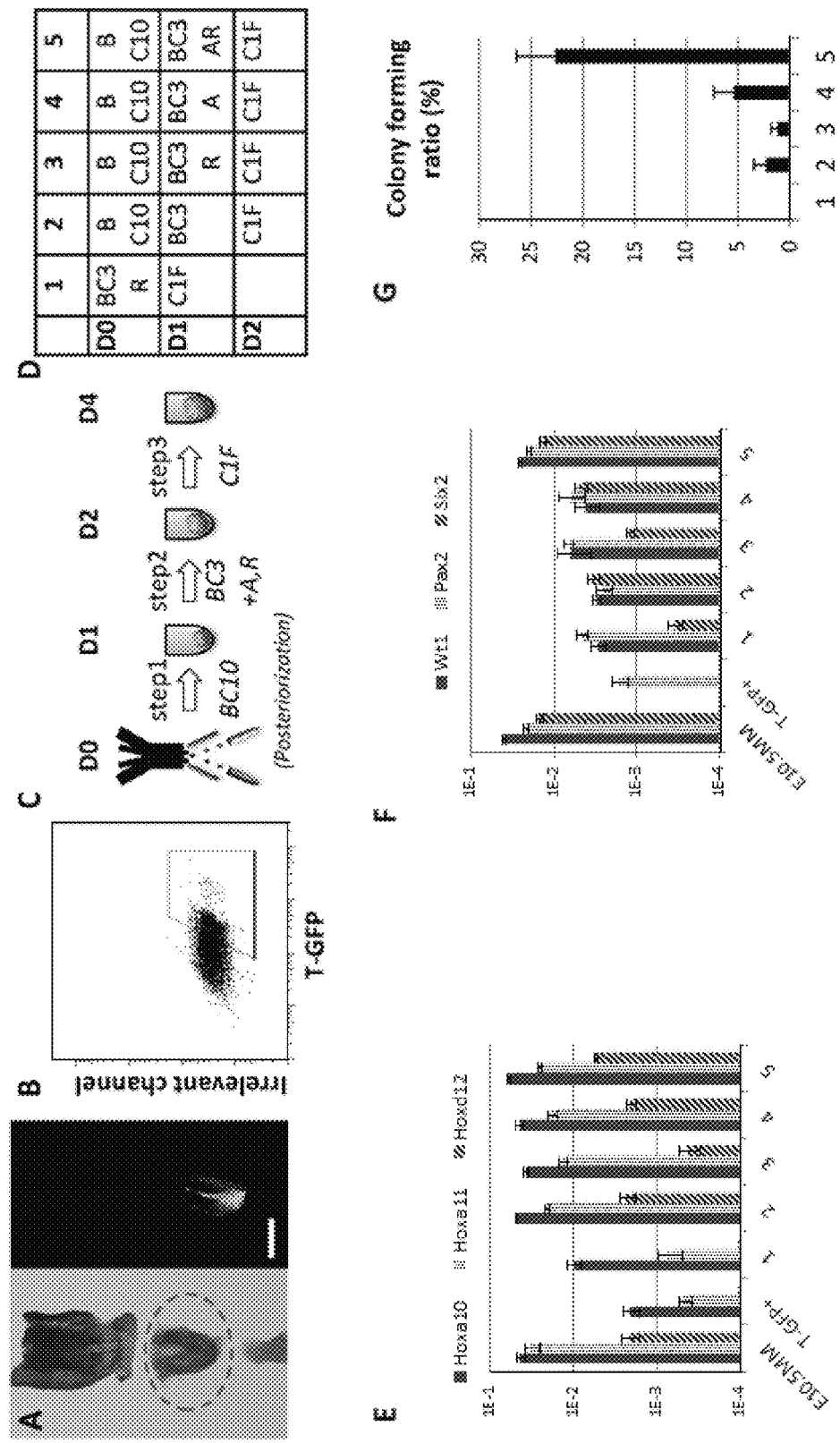
FIG. 22 is the results of the induction of metanephric nephron precursors from the T-positive posterior mesoderm at E8.5. A shows the T-GFP expression at an E8.5 embryo, a left panel is a bright-field, and a right panel is fluorescence (scale bar: 500 μm). In addition, the undifferentiated mesoderm region before merogenesis is shown with a dashed line contour. B shows a gate for sorting of a T-GFP-positive cell population. C and D show the culturing conditions. B: Bmp4; C: CHIR99021; A: activin; R: retinoic acid; F: Fgf9. E and F express the relative expression of each transcript relative to the expression of β-actin by the mean±s.e.m. (n=4). E10.5MM shows the E10.5 metanephric mesenchyme, and T-GFP+ shows a sample at the time of induction initiation. G shows a colony formation ratio of cultured cell aggregates by the mean±s.e.m. (n=4).
Figure 23:
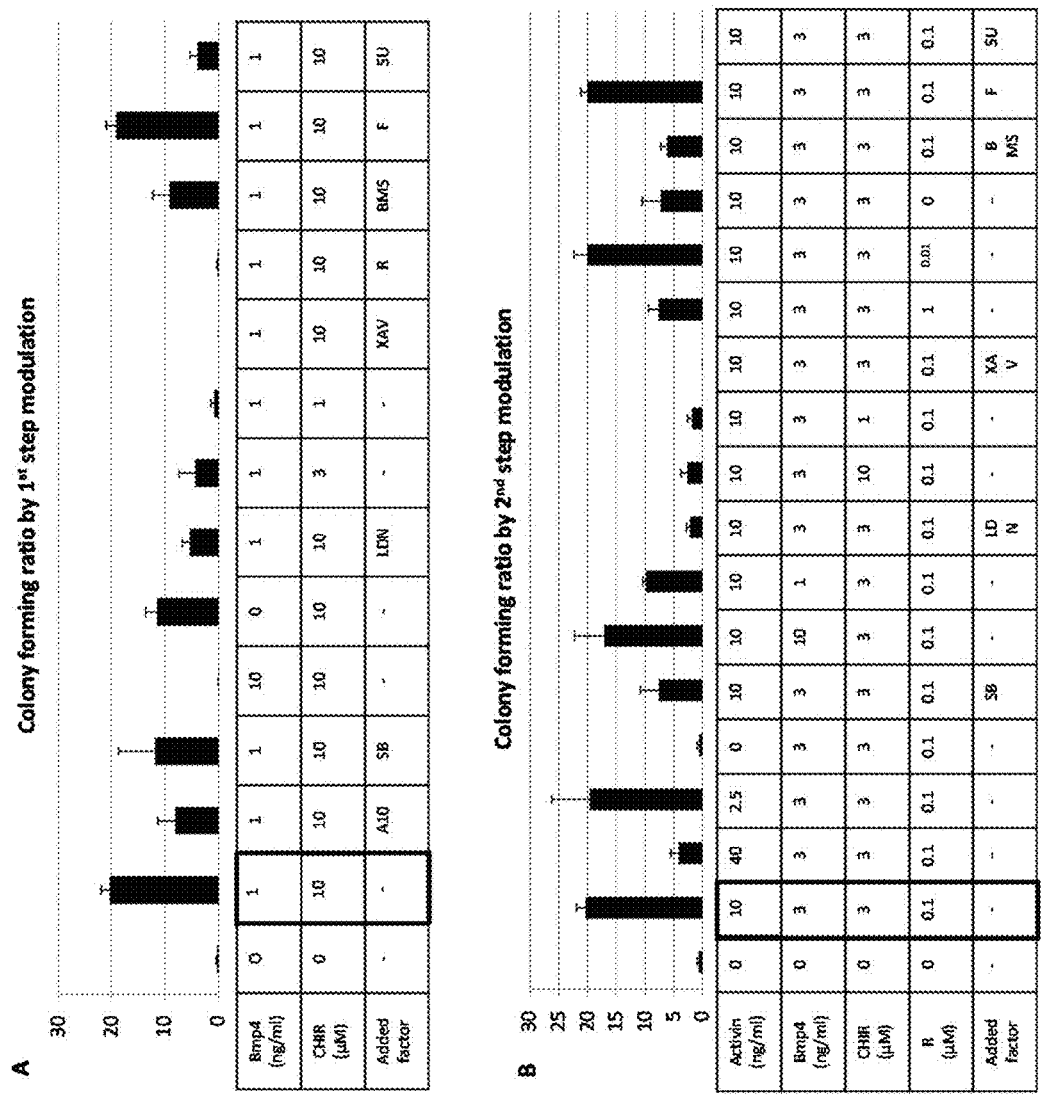
FIG. 23 is the results of the induction of nephron progenitor cells from the E8.5 posterior undifferentiated mesoderm. A is the results of the effect of a growth factor at a posteriorization stage or an inhibitor thereof, which was analyzed by a colony formation assay. A ratio of colony formation under each condition is shown as the mean±s.e.m. (n=3). The final adoption condition is a column which is second from left. B is the results of the effect of a growth factor at a renal cocktail stage or an inhibitor thereof, which was analyzed by a colony formation assay. A ratio of colony formation under each condition is shown as the mean±s.e.m. (n=3). The final adoption condition is a column which is second from left. Under all conditions, Y27632 (ROCK inhibitor) is contained. CHIR: CHIR99021 (canonical Wnt agonist); A10: 10 ng/ml activin; SB: SB431542 (Smad2/3 inhibitor); LDN: LDN93189 (Smad1/5/8 antagonist); XAV: XAV939 (Wnt signal antagonist), R: 0.1 μM retinoic acid; BMS: BMS493 (pan-RAR antagonist), F: 5 ng/ml Fgf9; SU: SU5402 (Fgfr1 inhibitor).

Based on the lineage tracing experiments, metanephric nephron progenitors were induced by using the sorted E8.5 T+ posterior mesoderm as the starting material. The results are shown in FIG. 18. The sorted cells were re-aggregated to form spheres and treated with various growth factors, followed by treatment with C1F as described above (FIG. 22C; step 3). Since the posterior intermediate mesoderm was marked by expressions of Osr1, Wt1 and posterior Hox genes, the inventors first focused on the growth factors that may affect the expressions of these genes. Synergistic effects of Bmp and Wnt signaling have been reported on the expressions of posterior Hox genes in mouse embryonic stem (ES) cell differentiation, and retinoic acid signaling is reported to be important for the expressions of Wt1 homologues in zebrafish development. Since simultaneous introduction of retinoic acid, Bmp and the Wnt agonist did not increase the posterior Hox genes to the levels observed in the embryonic metanephric mesenchyme (FIGS. 22D and 22E), a "posteriorization phase" was added. As canonical Wnt signals are reportedly important for caudal body extension, a high concentration of the Wnt agonist (10 μM CHIR) in combination with Bmp4 was added. This treatment (BC10; step 1) dramatically increased the expressions of posterior Hox genes, and it was able to detect colony formation from the induced cells, although the expression levels of nephric genes were still lower than those in the embryonic metanephric mesenchyme (FIGS. 22D and 22G). The inventors tried various conditions and found that the combination of activin and retinoic acid, together with Bmp4 and 3 μM CHIR (ABC3R; step 2) substantially increased the expressions of nephric genes (FIG. 22F). In this optimized three-step condition (BC10 followed by ABC3R and C1F), the cells formed higher numbers of colonies (22.7±3.66%, n=4), compared with single addition of either activin or retinoic acid (FIG. 22G). In the first posteriorization step, the concentration of the canonical Wnt agonist was critically important and addition of retinoic acid completely inhibited the colony-forming progenitor induction (FIG. 23A). In the second step, inhibition of any one of activin, retinoic acid, Bmp, Wnt or Fgf signaling resulted in a decrease in colony formation (FIG. 23B), suggesting that all of these signals were essential.

Figure 24:
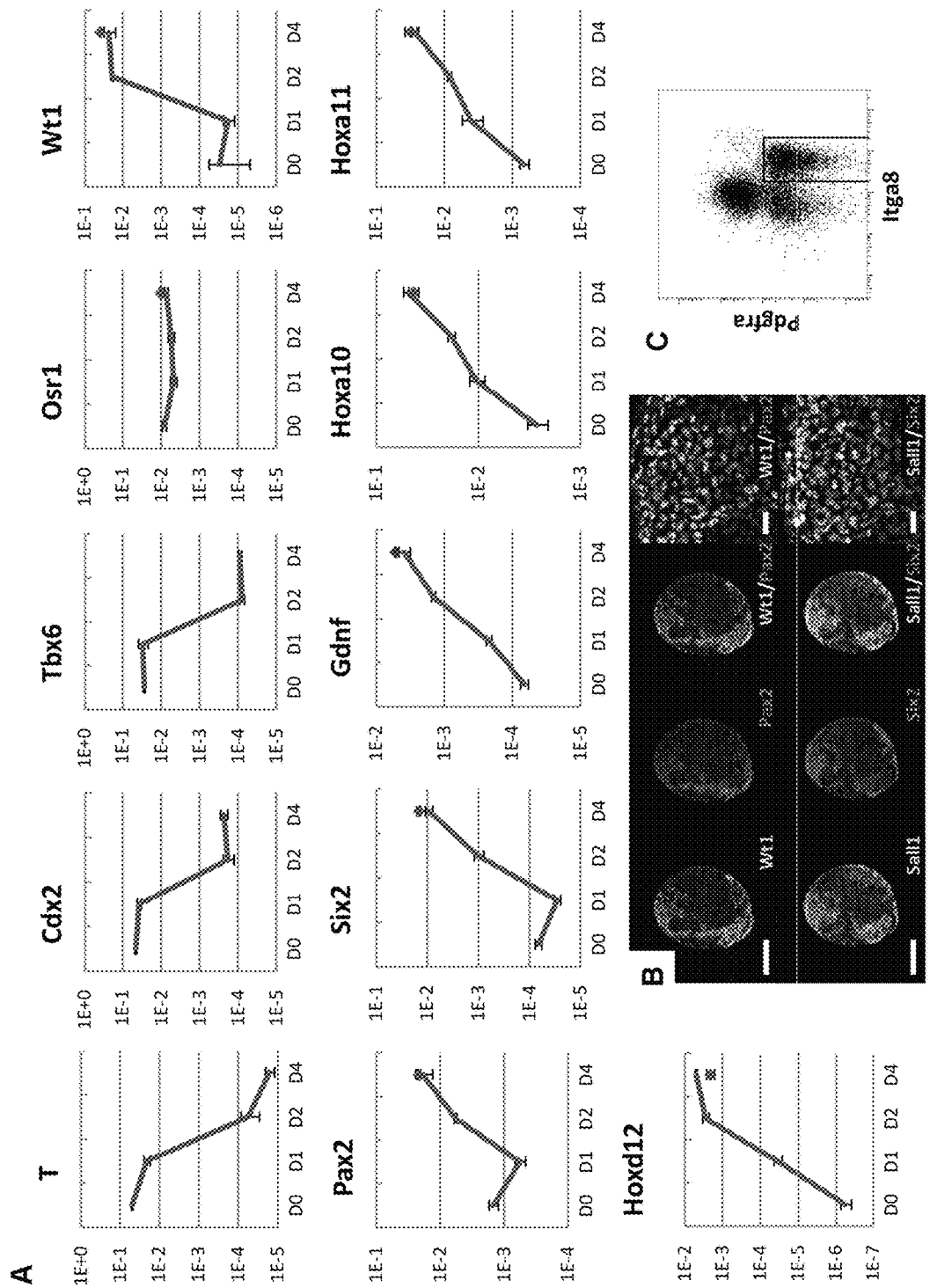
FIG. 24 is the results of conformation of the expression of a marker gene in the induction of metanephric nephron progenitor cells from the T-positive posterior mesoderm at E8.5. A is the results of conformation of dynamics of the temporal expression of a marker gene. The expression level of the embryonic metanephric mesenchyme at E10.5 is shown with a rhomboidal symbol. The relative expression of each transcript relative to the β-actin expression is shown by the mean±s.e.m. (n=4). B is the results of immunostaining of induced cell aggregates. A high magnification image is shown in right two panels. A scale bar is 200 μm (left six panels), and 20 micron (right end two panels). C is the results of FACS analysis of the Itga8/Pdgfra expression on the induction $4^{th}$ day (day 4).

The temporal kinetics of the gene expressions at every step of the induction process was further examined. The results are shown in FIG. 24. As shown in FIG. 24A, in the first step, T, Cdx2 and Tbx6, all of which are posterior mesoderm markers, were expressed and maintained, while posterior Hox genes started to increase. In the second step, nephric genes started to be expressed, and in the final step, the expressions of Pax2, Six2, Gdnf and posterior Hox genes increased to the levels in the embryonic metanephric mesenchyme. It was further confirmed the co-localization of multiple transcription factors in single cells, such as Wt1/Pax2 and Sall1/Six2 (FIG. 24B), and the existence of the Itga8+/Pdgfra− population (30.8±2.4%, n=4) in the induced spheres (FIG. 24C). Taken together, a protocol to induce metanephric nephron progenitors from the posterior nascent mesoderm was established.

Example 6: Metanephric Nephron Progenitor Induction from Mouse ES Cells

Figure 25:
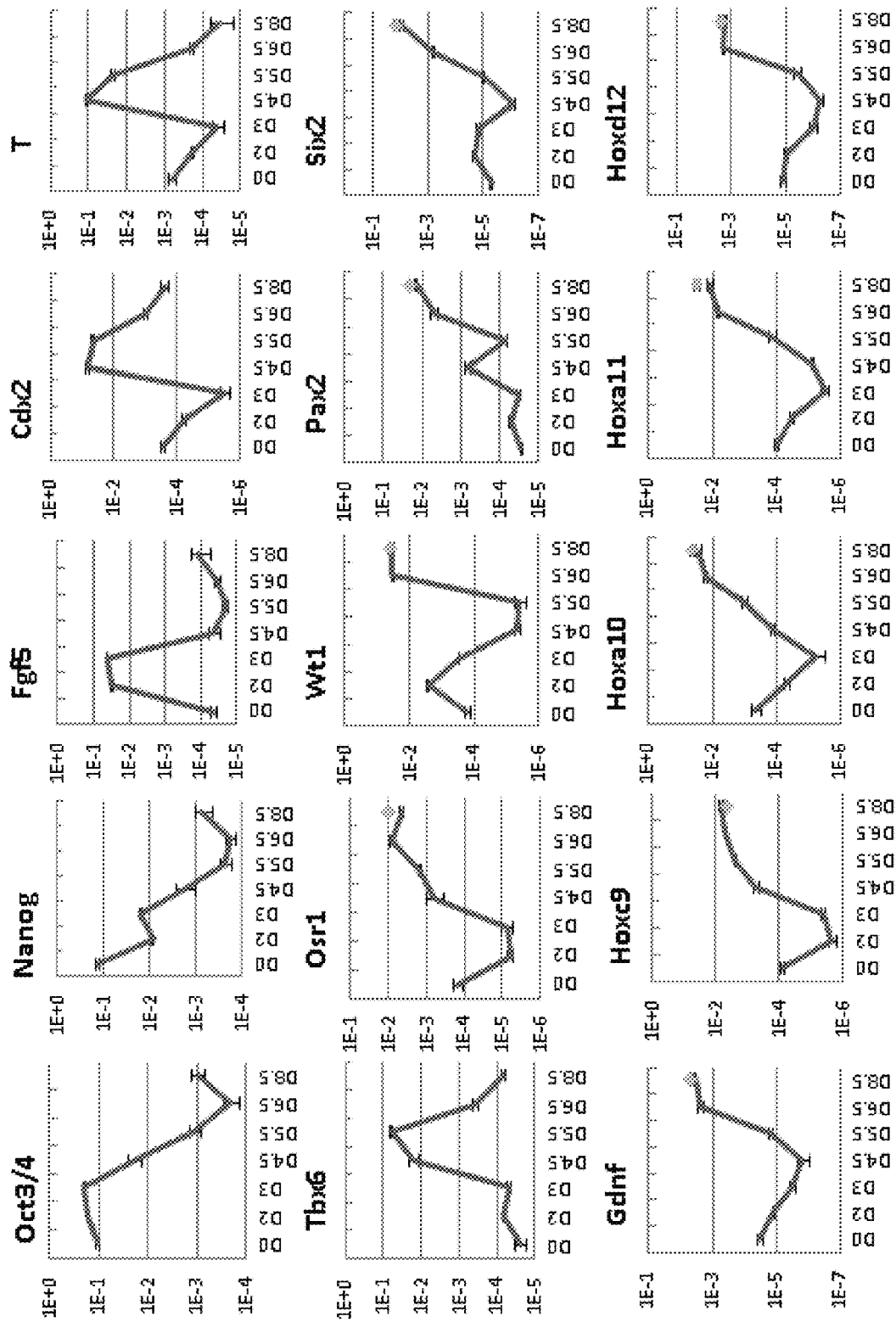
FIG. 25 shows kinetics of the gene expression at each stage of the induction of nephron progenitor cells from mouse ES cells. The expression level in the E10.5 embryonic metanephric mesenchyme is shown with a rhomboidal symbol. The gene expression is shown by the relative expression of each transcript relative to the β-actin expression (mean±s.e.m.) (n=4).
Figure 26:
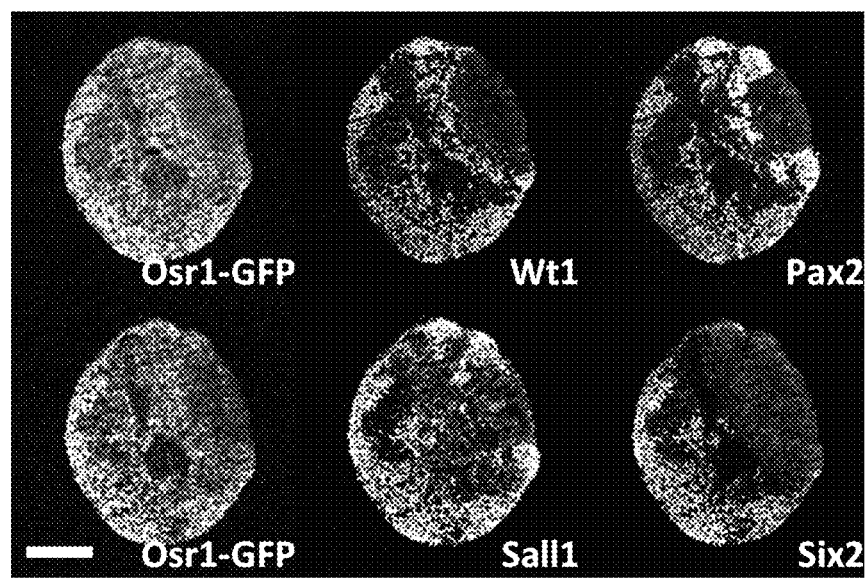
FIG. 26 shows localization of Osr1-GFP/Wt1/Pax2- and Osr1-GFP/Sall1/Six2-positive cells in the induced embryoid body at day 8.5 in the induction of metanephric nephron progenitor cells from mouse ES cells. A scale bar is 200 μm (left six panels).
Figure 27:
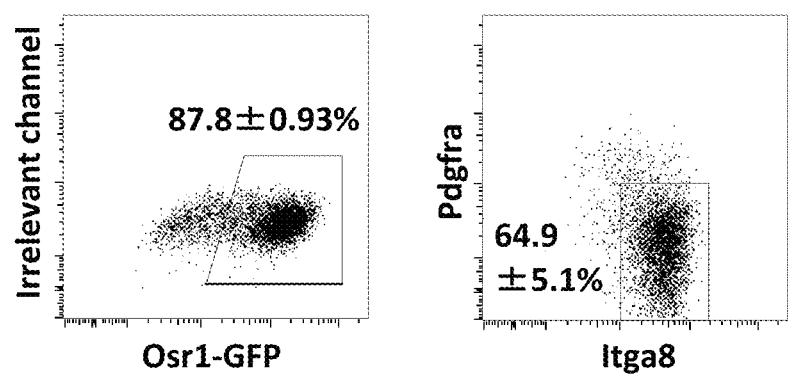
FIG. 27 shows the results of FACS analysis of the Osr1-GFP and Itga8/Pdgfra expression in the embryoid body at day 8.5 in the induction of nephron progenitor cells from mouse ES cells.

Next, induction of metanephric nephron progenitors from ES cells was carried out. An outline of the entire step of inducing the metanephric nephron progenitor cell from the mouse ES cell is shown in FIG. 1, and the gene expression of signature genes at each stage is shown in FIG. 25. To monitor the induction of intermediate mesoderm and metanephric nephron progenitors, the Osr1-GFP ES cell line, from which the Osr1-GFP mice was generated described above, was used. Embryoid bodies (EBs) were generated in serum-free medium without any factors for 2 days. metanephric nephron progenitors were generated by using EBs. During the following 24 h, a low concentration of activin induced transient expression of the epiblast marker Fgf5. The EBs were subsequently treated with Bmp4 and a high concentration of CHIR (step 2). At day 4.5, the expressions of T, as well as Cdx2 and Tbx6, which represent the posterior nascent precursor, were up-regulated. Subsequently, the inventors completely mimicked the protocol for the embryonic posterior mesoderm (FIG. 22C and steps 3-5 of FIG. 1). The induced EBs harvested at day 8.5 expressed multiple signature genes for metanephric nephron progenitors at comparable levels to the embryonic metanephric mesenchyme (FIG. 25). Immunostaining showed that many cells co-expressed typical nephrogenic transcription factors, including Osr1, Wt1, Pax2, Sall1 and Six2 (FIG. 26). Furthermore, FACS analyses showed that nearly 90% of the cells were Osr1-GFP+, and among the Osr1+ cells, Itga8+/Pdgfra− progenitors constituted approximately 65% (FIG. 27). These induced progenitors exhibited robust colony formation (21.3±1.69%, n=8). Therefore, this shows that the inventors succeeded in generating metanephric nephron progenitors from ES cells.

Example 7: Formation of Three-Dimensional Kidney Structures by ES Cells

Figure 28:
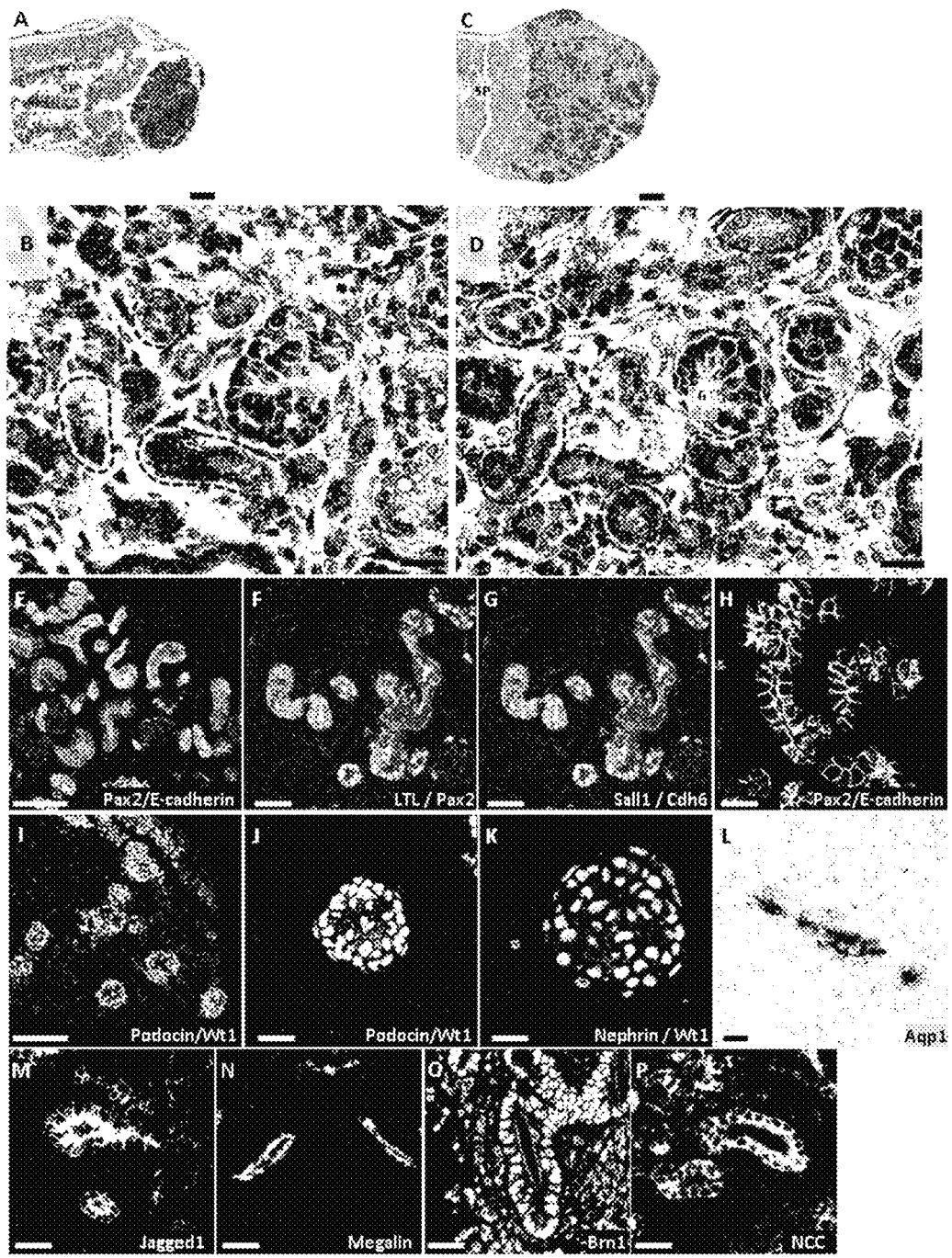
FIG. 28 shows the results of the induction of the kidney having the three-dimensional structure from mouse ES cells. A to D are the results of hematoxylin and eosin staining (B and D: high magnification). A and B are the embryonic metanephric mesenchyme, and C and D are the embryoid body which was induced by coculturing with spinal cord. The renal tubule of the kidney is shown with a dashed line contour. SP: spinal cord, G: glomerulus. A scale bar is 200 μm and 20 μm. E to P are the results of immunostaining of the induced embryoid body with a renal tubule marker (E~H, L~P) (proximal renal tubule marker: LTL, distal renal tubule marker: E-cadherin, Brn1 and NCC) and a glomerulus marker (I~K). A scale bar is 100 μm (E, I) and 20 μm (F~H, J~L).

It is well established that the metanephric mesenchyme from E11.5 embryos undergoes mesenchymal-to-epithelial transition and forms glomeruli and renal tubules when co-cultured with embryonic spinal cords or Wnt4-expressing cells at the air-liquid interface (Non-Patent Literature 8: Kispert et al., Development 125, 4225-234, 1998). The glomeruli and renal tubules formed by E11.5 embryos are shown in FIG. 28A. Therefore, the induced EBs of Example 6 was cultured in the same manner, which resulted in robust tubulogenesis. The results are shown in FIGS. 28C and 28D. Specifically, histological examination of EBs harvested at day 6 identified many tubules under both conditions (FIGS. 28C and 28D), which was confirmed by E-cadherin staining (FIG. 28E). Most of the tubules were positive for Pax2 and Sall1, indicating that they were renal tubules (FIGS. 28E-H, L-P). Some tubules expressed markers of proximal tubules, such as LTL or Cadherin6, Aquaporin1, Jagged1, Megalin (FIGS. 28F, G, L-N). Other tubules showed expressions of E-cadherin, Brn1 and NCC, indicative of distal tubule formation (FIGS. 28H, O, P). More impressively, numerous glomerulus-like structures were observed (FIGS. 28C, and 28I-K). These structures contained clusters of cells that expressed a typical podocyte marker, Wt1, in their nuclei, as well as foot process proteins such as nephrin and podocin. These structures were indistinguishable from those of the embryonic metanephric mesenchyme (FIGS. 28B and D, n=6).

Figure 29:
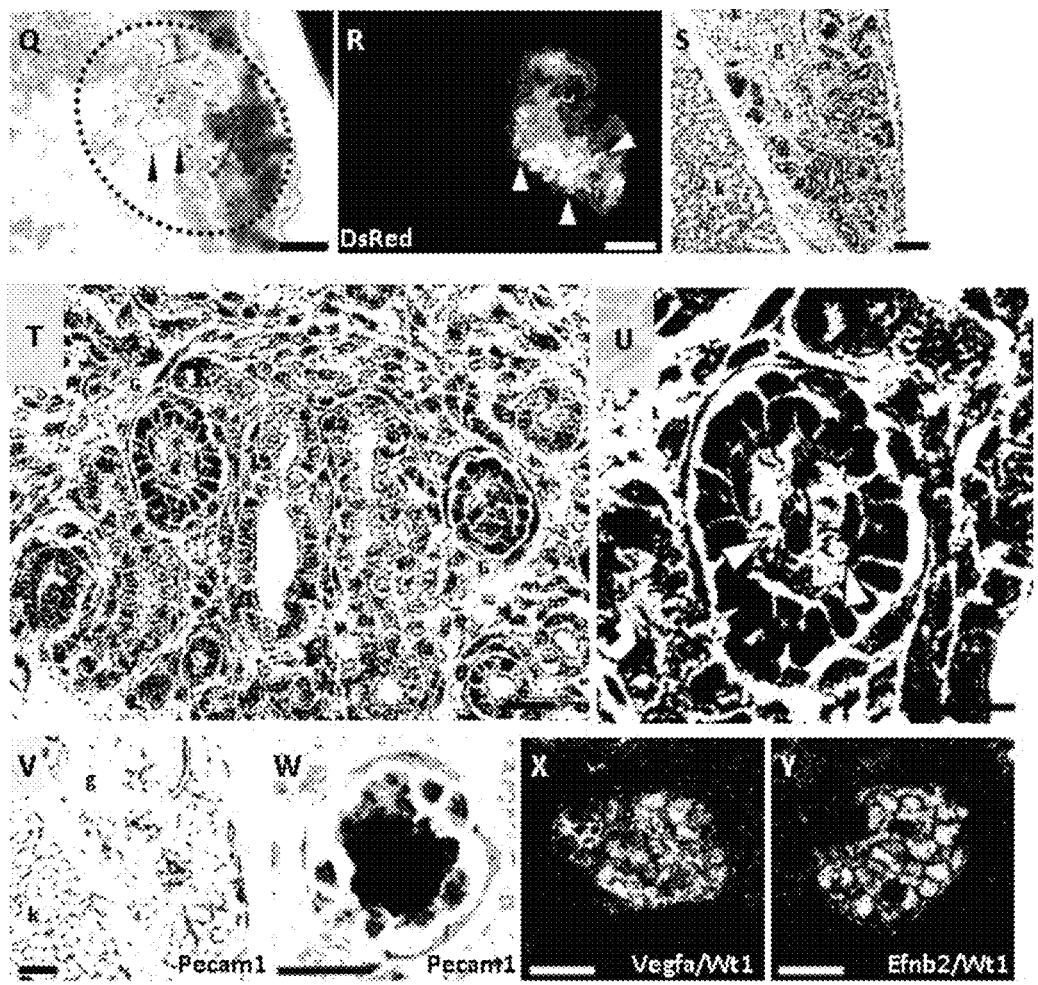
FIG. 29 shows the results of the induction of the three-dimensionally structured kidney from mouse ES cells. Q and R show the mouse kidney obtained by transplanting the induced embryoid body beneath the kidney capsule of a nude mouse, and isolating the kidney after one week. A contour of the graft is drawn with a dashed line. A black arrow of Q shows vascularization of the graft. R is a fluorescent image of the graft. A white arrow of R shows a nephron-like structure in the graft. A scale bar is 500 μm. S to U are the results of hematoxylin and eosin staining of the transplanted kidney section. S is a low magnification image (g: graft; k: kidney of host, scale bar: 100 μm). T is an intermediate magnification image (A contour of the renal tubule of the kidney is drawn with a dashed line, G: glomerulus, scale bar: 20 μm). U is a high magnification image of the glomerulus in the graft (An arrow shows an erythrocyte in the vasculature which invades the glomerulus, scale bar: 20 μm). V and W are the results of immunostaining with Pecam1 which is a blood vessel marker (V: low magnification image, W: high magnification image of the glomerulus in the graft, g: graft, k: kidney of host, scale bar: 20 μm). X and Y show the expression of a blood vessel inducing factor (X: Vegfa, Y: Efnb2) in the podocyte.

Another ES cell line with ubiquitous expression of DsRed was used, and the induced EBs were transplanted beneath the kidney capsule of immunodeficient mice, together with spinal cords (FIGS. 29 Q and 29R). When harvested after 1 week, the rudiments had undergone massive tubulogenesis, similar to the in vitro cultures (FIGS. 29S and 29T). Furthermore, many blood vessels had integrated into the transplanted tissue, most notably into the ES cell-derived glomeruli (FIGS. 29Q and 29U-W). It was confirmed that these glomeruli actually expressed Vegfa and Efnb2, which are angiogenesis factors (FIGS. 29X and 29Y). The integrated blood vessels originated from the host animals, because they were negative for DsRed, indicating that the transplanted glomeruli could become connected to the host circulation, which is an essential requirement for the glomerular function as a filtration apparatus.

Example 8: Induction of Metanephric Nephron Progenitor from Human iPS Cells

Figure 30:
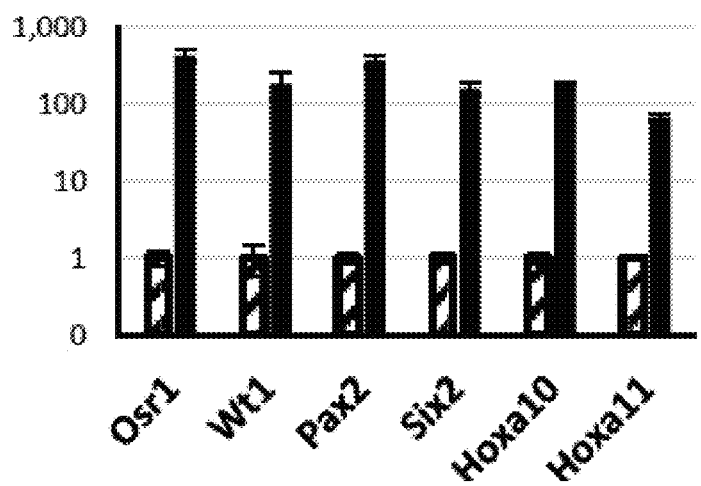
FIG. 30 is the results of gene expression analysis of differentiated iPS cells, in the induction of metanephric nephron progenitor cells from human iPS cells. The relative expression of each transcript relative to immature iPS cells (each left row) is shown by the mean±s.e.m. (n=6).
Figure 31:
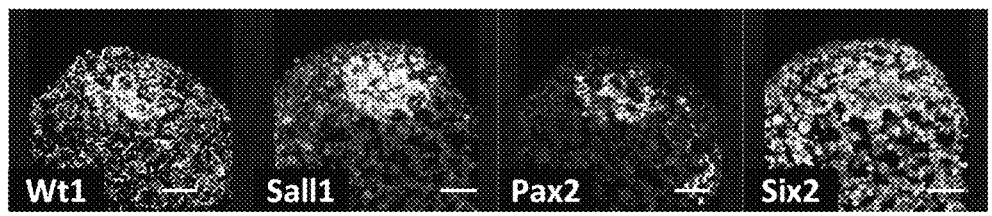
FIG. 31 shows localization of Wt1/Pax2- and Sall1/Six2-positive cells in the induced embryoid body at day 14 ($14^{th}$ day), in the induction of metanephric nephron progenitor cells from human iPS cells. A scale bar is 75 μm.
Figure 32:
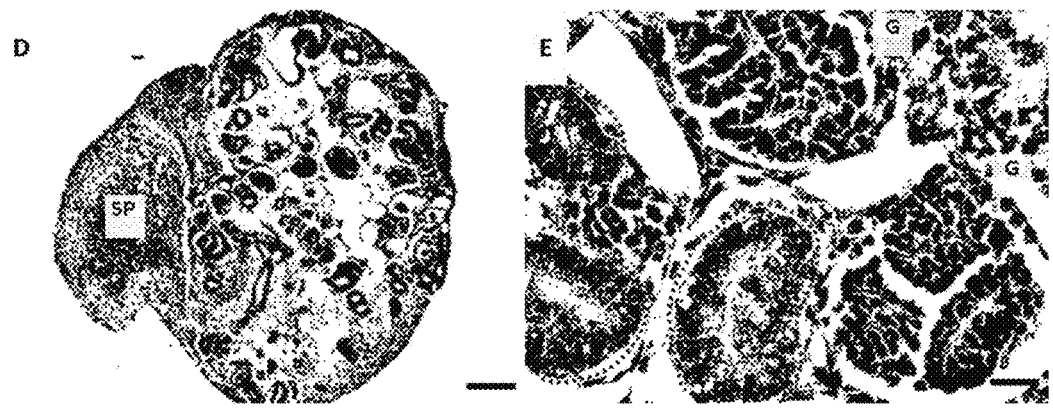
In FIGS. 32, D and E are the results of hematoxylin and eosin staining of the embryoid body which was induced by coculturing with spinal cord (E is high magnification image). A contour of the renal tubule is drawn with a dashed line. SP: spinal cord, G: glomerulus, scale bar: 200 μm (D) and 20 μm (E). F to K are the results of immunostaining of the adjacent section of the induced embryoid body. K is a glomerulus marker, H and I are a renal tubule marker, and a scale bar is 50 μm.
Figure 32:
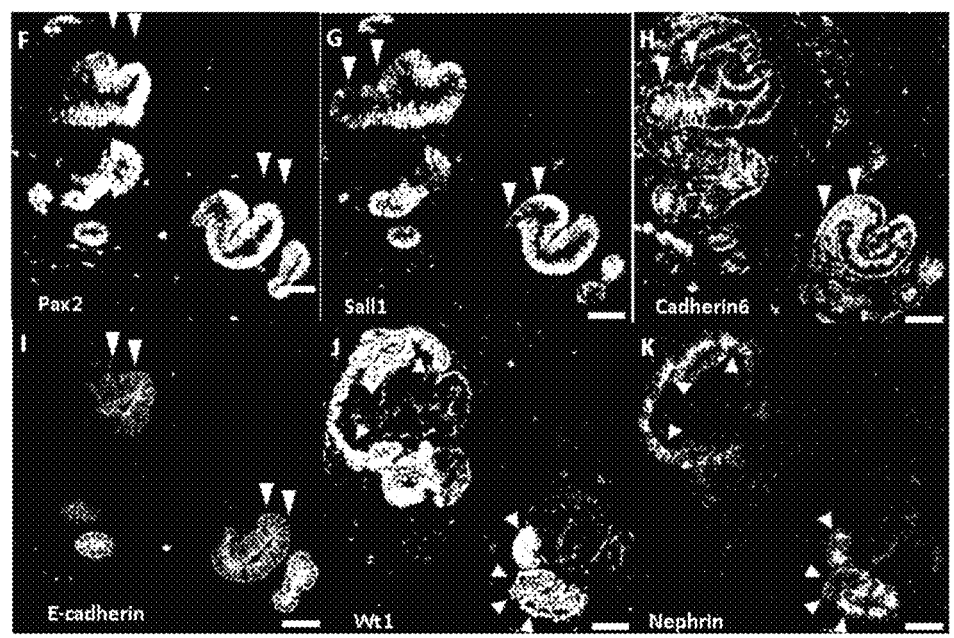

The above protocol for mouse ES cells was applied to human iPS cell for differentiation toward metanephric nephron progenitors in vitro. Previous reports showed the importance of Bmp, Fgf and activin signals for the initial induction of mesodermal lineage cells for human pluripotent stem cells (Non-Patent Literature 19: Bernard et al., Cell Stem Cell 9, 144-155, 2011; Non-Patent Literature 20: Kattman et al., Cell Stem cell 8, 228-240, 2011; Non-Patent Literature 21: Yu et al., Cell Stem Cell 8, 326-334, 2011). Therefore, human iPS cell aggregates were treated with Bmp for the initial 24 h, followed by activin and Fgf for the next 2 days. The induced mesodermal cells were further posteriorized and maintained in the immature mesoderm state in the presence of a high concentration of Wnt agonist (CHIR 10 μM) and Bmp, similar to mouse ES cell induction. Given the physiological time period for caudal body extension in human embryos, EBs were cultured under these culture conditions for 6 days. Subsequently, the inventors completely mimicked the protocol for mouse ES cell differentiation by simply adjusting the culture periods. The induced EBs harvested at day 14 expressed multiple signature genes for metanephric nephron progenitors (FIG. 30). Immunostaining revealed that many cells coexpressed typical nephrogenic transcription factors, including Wt1, Pax2, Sall1 and Six2 (FIG. 31). These induced progenitors exhibited robust tubulogenesis and clustered podocyte formation when cocultured with mouse embryonic spinal cords (FIGS. 32D and 32E, n=6). Immunohistochemical examinations at day 10 revealed the formation of well-specified nephron components. These structures consisted of Wt1/nephrin-positive glomeruli (FIGS. 32K and 32J), cadherin6-positive proximal tubules (FIG. 32H) and E-cadherin-positive distal tubules (FIG. 32I), all of which appeared to be connected in that order, thereby mimicking human embryonic kidney formation.

Figure 33:
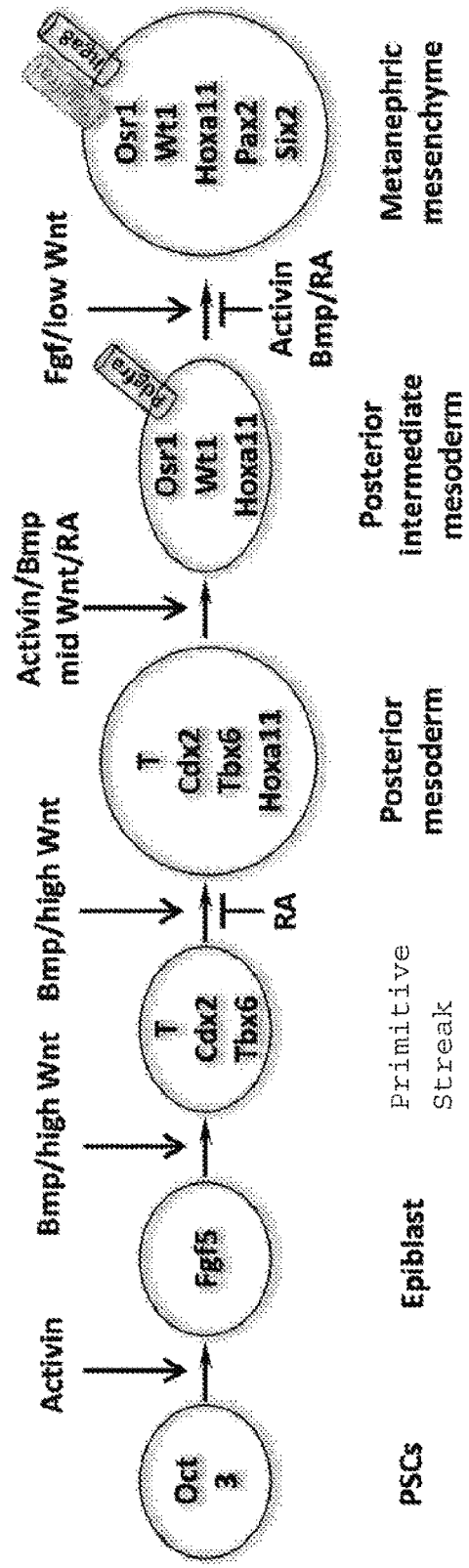
FIG. 33 is a model of the differentiation-induction from pluripotent cells to the metanephric mesenchyme.

In conclusion, the inventors succeeded in the induction of bona fide metanephric nephron progenitors and three-dimensional kidney structures from both mouse and human pluripotent stem cells, by recapitulating the developmental processes in vivo (FIG. 33).

The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

According to the present invention, a pluripotent stem cell, for example, an ES cell or an iPS cell can be differentiation-induced into a metanephric nephron progenitor cell. In addition, the present invention can be used in formation of the three-dimensional kidney structure from the pluripotent stem cell, as a part of steps of the formation. Therefore, the present invention is useful in research and regenerative medicine utilizing the differentiation-induction from the pluripotent stem cell into the kidney.

The invention claimed is:

1. A method of differentiation-inducing a pluripotent stem cell derived from a mammal into a metanephric nephron progenitor cell, the method comprising the steps of:
   (a) culturing an embryoid body which has been induced from the pluripotent stem cell in a culture medium containing:
      wingless-type MMTV integration site family (Wnt) agonist at a high concentration (concentration A), and
      optionally bone morphogenetic protein (Bmp),
   to obtain a posterior mesoderm,
   (b) culturing the posterior mesoderm in a culture medium containing:
      Bmp,
      activin,
      retinoic acid, and
      Wnt agonist at an intermediate concentration (concentration B),
   to obtain a posterior intermediate mesoderm, and
   (c) culturing the posterior intermediate mesoderm in a culture medium containing:
      fibroblast growth factor (Fgf), and
      Wnt agonist at a low concentration (concentration C),
   to obtain the metanephric nephron progenitor cell expressing Paired box gene 2 (Pax2), Six2, Glial cell-derived neurotrophic factor (Gdnf), Homeobox protein a10 (Hoxa10), Hoxa11 and Hoxd12 genes in this order,
      wherein a concentration of the Wnt agonist is concentration A>concentration B>concentration C, and a concentration A is at least five times of a concentration C, wherein the pluripotent stem cell is a mouse embryonic stem (ES) cell or a mouse induced pluripotent stem (iPS) cell, or a human ES cell or a human iPS cell.

2. The differentiation-inducing method according to claim 1, wherein the concentrations of the Wnt agonist in the steps (a), (b) and (c) are such that a concentration A is at least three times of a concentration B, and a concentration B is at least three times of a concentration C.

3. The differentiation-inducing method according to claim 1, wherein the Wnt agonist is a glycogen synthase kinase 3 (GSK-3) inhibitor, provided that Wnt agonists at respective steps may be same or different.

4. The differentiation-inducing method according to claim 3, wherein the Wnt agonist is selected from the group consisting of CHIR99021, 6-bromoindirubin-3'-oxime (BIO), and SB415286, provided that Wnt agonists at respective steps may be the same or different.

5. The differentiation-inducing method according to claim 4, wherein the Bmp is Bmp4, and the Fgf is Fgf9.

6. The differentiation-inducing method according to claim 3, wherein the Bmp is selected from the group consisting of Bmp2, Bmp4 and Bmp7, and the Fgf is selected from the group consisting of Fgf2, Fgf9 and Fgf20.

7. The differentiation-inducing method according to claim 1, wherein the Wnt agonist in the steps (a), (b) and (c) is CHIR99021, and a concentration A is 7.5 µM to 15 µM, and a concentration C is 0.5 µM to 2.0 µM.

8. The differentiation-inducing method according to claim 7, wherein the Bmp in the steps (a) and (b) is Bmp4, and a concentration thereof in the step (a) is 0.1 ng/ml to 3 ng/ml, and a concentration thereof in the step (b) is 1 ng/ml to 10 ng/ml.

9. The differentiation-inducing method according to claim 8, wherein activin is contained at a concentration of 2.5 to 40 ng/mL, in the step (b).

10. The differentiation-inducing method according to claim 1, wherein the steps (a), (b) and (c) are continuous steps.

11. The differentiation-inducing method according to claim 1, wherein the medium in the step (c) contains none of Bmp, retinoic acid and activin.

12. The differentiation-inducing method according to claim 1, wherein the pluripotent stem cell is a human iPS cell.

13. The differentiation-inducing method according to claim 1, wherein the pluripotent stem cell is the mouse ES cell or the mouse iPS cell, and the step (a) is a step of culturing the embryoid body for a period of 1-4 days.

14. The differentiation-inducing method according to claim 1, wherein the pluripotent stem cell is the human ES cell or the human iPS cell, and the step (a) is a step of culturing the embryoid body for a period of 3-11 days.

* * * * *